US012584917B2

(12) United States Patent

Yang et al.

(10) Patent No.: US 12,584,917 B2

(45) Date of Patent: Mar. 24, 2026

(54) RECOMBINANT ANTIBODIES, KITS COMPRISING THE SAME, AND USES THEREOF

(71) Applicant: Academia Sinica, Taipei City (TW)

(72) Inventors: An-Suei Yang, Taipei City (TW); Chao-Ping Tung, Taipei City (TW); Chung-Ming Yu, New Taipei City (TW); Chi-Yung Chen, Taipei City (TW); Yu-Chuan Huang, Taipei City (TW); Pei-Hsun Tsai, Taipei City (TW); Szu-Yu Lin, Taipei City (TW); Hung-Ju Hsu, Taipei City (TW); Hung-Pin Peng, Taipei City (TW); Fei-Hung Hung, Taipei City (TW)

(73) Assignee: Academia Sinica, Taipei City (TW)

( * ) Notice: Subject to any disclaimer, the term of this patent is extended or adjusted under 35 U.S.C. 154(b) by 681 days.

(21) Appl. No.: 17/922,590

(22) PCT Filed: May 4, 2021

(86) PCT No.: PCT/US2021/030702
§ 371 (c)(1),
(2) Date: Oct. 31, 2022

(87) PCT Pub. No.: WO2021/226123

PCT Pub. Date: Nov. 11, 2021

(65) Prior Publication Data

US 2023/0168249 A1 Jun. 1, 2023

Related U.S. Application Data

(60) Provisional application No. 63/020,775, filed on May 6, 2020.

(51) Int. Cl.
*G01N 33/569* (2006.01)
*C07K 16/10* (2006.01)

(52) U.S. Cl.
CPC ... *G01N 33/56983* (2013.01); *C07K 16/1002* (2023.08); *C07K 16/1003* (2023.08); *C07K 2317/622* (2013.01); *C07K 2317/92* (2013.01); *G01N 2333/165* (2013.01); *G01N 2469/10* (2013.01); *G01N 2470/04* (2021.08)

(58) Field of Classification Search
None
See application file for complete search history.

(56) References Cited

FOREIGN PATENT DOCUMENTS

| WO | WO-2005018538 A2 | * | 3/2005 | ......... C07K 16/1002 |
| WO | WO-2008060331 A2 | * | 5/2008 | .......... C07K 14/005 |
| WO | WO-2009128963 A2 | * | 10/2009 | ............. A61P 31/14 |

OTHER PUBLICATIONS

Berry et al., Journal of Virological Methods, 2004, 120;87-96. (Year: 2004).*
Duan et al., Biochemical and Biophysical Research Communications, 2005, 333:186-193. (Year: 2005).*
Tu et al., Emerging Infectious Diseases, 2004. 10(12):2244-2248. (Year: 2004).*

* cited by examiner

*Primary Examiner* — Nicole Kinsey White

(74) *Attorney, Agent, or Firm* — NZ Carr Law Office

(57) ABSTRACT

Disclosed herein are recombinant antibodies or the fragment thereof for detecting severe acute respiratory syndrome coronavirus (SARS-CoV). According to some embodiments, the SARS-CoV is SARS-CoV-1. According to some alternative embodiments, the SARS-CoV is SARS-CoV-2. Also disclosed herein are a kit comprising the recombinant antibodies, and a method for diagnosing the infection of SARS-CoV by using the recombinant antibody or the kit.

8 Claims, 1 Drawing Sheet

Specification includes a Sequence Listing.

RECOMBINANT ANTIBODIES, KITS COMPRISING THE SAME, AND USES THEREOF

CROSS-REFERENCE TO RELATED APPLICATIONS

This application is a U.S. National Stage Filing under 35 U.S.C. 371 from International Patent Application Serial No. PCT/US21/30702, filed May 4, 2021, and published on Nov. 11, 2021, which claims the priority of U.S. Ser. No. 63/020, 775, filed May 6, 2020, the disclosure of which are incorporated by reference herein in their entireties.

BACKGROUND OF THE INVENTION

1. Field of the Invention

The present disclosure in general relates to the field of disease diagnosis. More particularly, the present disclosure relates to recombinant antibodies and the uses thereof in diagnosing the infection of severe acute respiratory syndrome coronavirus (SARS-CoV), especially SARS-CoV-2.

2. Description of Related Art

SARS-CoV-2 outbreak in late-2019 in Wuhan China has led to global COVID-19 (coronavirus infectious disease 2019) pandemic, declared by the World Health Organization (WHO) in Mar. 11, 2020. As of Apr. 25, 2021, the pandemic has already affected more than 220 countries/regions, and resulted in at least 146,054,107 confirmed cases, including 3,092,410 deaths, according to the COVID-19 Dashboard of World Health Organization (WHO). To many countries and regions so far, the SARS-CoV-2 outbreak has been proven to be an unprecedented catastrophe in health, social and economic aspects. In the worst-case future scenario, the SARS-CoV-2 outbreak would continue impacting the majority of countries, especially the low-income countries with limited resources, due to difficulties in mitigating the burden associated with the viral infections.

Large scale and wide spread detections of the SARS-CoV-2 infections become essential to contain the spread of the pandemic, considering that prevention is the best practice to reduce the impact of the pandemic before effective treatment and vaccine becoming available to the general public. The majority of molecular-based detection procedures made available so far for SARS-CoV-2 are real-time reverse transcriptase PCR assays (RT-PCR). Alternatively, immunoassays of the viral antigens are powerful technologies for rapid and quantitative/semi-quantitative molecular detections. In particular, lateral flow immunoassays (LFIAs) are compatible with the WHO ASSURED (affordable, sensitive, specific, user-friendly, rapid and robust, equipment free and deliverable) guidelines. However, so far, there have only been a few of these tests commercialized for SARS-CoV-2 antigen detection and normally require a high viral count to work effectively.

In view of the foregoing, there exists in the related art a need for an antibody with sufficient specificity and affinity to SARS-CoV-2 so as to establish a diagnostic platform for infection prevention and/or treatment purposes.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, the first aspect of the disclosure is directed to a recombinant antibody or the fragment thereof. According to embodiments of the present disclosure, the recombinant antibody or the antibody fragment comprises a light chain variable (VL) region and a heavy chain variable (VH) region, in which the VL region comprises a first light chain complementarity determining region (CDR-L1), a second light chain CDR (CDR-L2), and a third light chain CDR (CDR-L3); and the VH region comprises a first heavy chain CDR (CDR-H1), a second heavy chain CDR (CDR-H2), and a third heavy chain CDR (CDR-H3).

According to some embodiments of the present disclosure, the CDR-L1, CDR-L2 and CDR-L3 respectively have amino acid sequences of SEQ ID NOs: 1-3, and the CDR-H1, CDR-H2 and CDR-H3 respectively have amino acid sequences of SEQ ID NOs: 4-6. According to some preferred embodiments, the VL region comprises an amino acid sequence at least 85% identical to SEQ ID NO: 43, and the VH region comprises an amino acid sequence at least 85% identical to SEQ ID NO: 44. In some working examples, the VL and VH regions of the recombinant antibody or the antibody fragment respectively comprise amino acid sequences 100% identical to SEQ ID NOs: 43 and 44.

According to certain embodiments of the present disclosure, the CDR-L1, CDR-L2 and CDR-L3 respectively have amino acid sequences of SEQ ID NOs: 7-9, and the CDR-H1, CDR-H2 and CDR-H3 respectively have amino acid sequences of SEQ ID NOs: 10-12. According to some preferred embodiments, the VL region comprises an amino acid sequence at least 85% identical to SEQ ID NO: 45, and the VH region comprises an amino acid sequence at least 85% identical to SEQ ID NO: 46. In some working examples, the VL and VH regions of the recombinant antibody or the antibody fragment respectively comprise amino acid sequences 100% identical to SEQ ID NOs: 45 and 46.

According to certain embodiments of the present disclosure, the CDR-L1, CDR-L2 and CDR-L3 respectively have amino acid sequences of SEQ ID NOs: 13-15, and the CDR-H1, CDR-H2 and CDR-H3 respectively have amino acid sequences of SEQ ID NOs: 16-18. According to some preferred embodiments, the VL region comprises an amino acid sequence at least 85% identical to SEQ ID NO: 47, and the VH region comprises an amino acid sequence at least 85% identical to SEQ ID NO: 48. In certain examples, the VL and VH regions of the recombinant antibody or the antibody fragment respectively comprise amino acid sequences 100% identical to SEQ ID NOs: 47 and 48.

According to some embodiments of the present disclosure, the CDR-L1, CDR-L2 and CDR-L3 respectively have amino acid sequences of SEQ ID NOs: 19-21, and the CDR-H1, CDR-H2 and CDR-H3 respectively have amino acid sequences of SEQ ID NOs: 22-24. According to the preferred embodiments, the VL region comprises an amino acid sequence at least 85% identical to SEQ ID NO: 49, and the VH region comprises an amino acid sequence at least 85% identical to SEQ ID NO: 50. In certain examples, the VL and VH regions of the recombinant antibody or the antibody fragment respectively comprise amino acid sequences 100% identical to SEQ ID NOs: 49 and 50.

According to some embodiments of the present disclosure, the CDR-L1, CDR-L2 and CDR-L3 respectively have amino acid sequences of SEQ ID NOs: 25-27, and the CDR-H1, CDR-H2 and CDR-H3 respectively have amino acid sequences of SEQ ID NOs: 28-30. According to some preferred embodiments, the VL region comprises an amino acid sequence at least 85% identical to SEQ ID NO: 51, and the VH region comprises an amino acid sequence at least 85% identical to SEQ ID NO: 52. In certain working examples, the VL and VH regions of the recombinant antibody or the antibody fragment respectively comprise amino acid sequences 100% identical to SEQ ID NOs: 51 and 52.

According to some embodiments of the present disclosure, the CDR-L1, CDR-L2 and CDR-L3 respectively have amino acid sequences of SEQ ID NOs: 31-33, and the CDR-H1, CDR-H2 and CDR-H3 respectively have amino acid sequences of SEQ ID NOs: 34-36. According to some preferred embodiments, the VL region comprises an amino acid sequence at least 85% identical to SEQ ID NO: 53, and the VH region comprises an amino acid sequence at least 85% identical to SEQ ID NO: 54. In some specific examples, the VL and VH regions of the recombinant antibody or the antibody fragment respectively comprise amino acid sequences 100/6 identical to SEQ ID NOs: 53 and 54.

According to certain embodiments of the present disclosure, the CDR-L1, CDR-L2 and CDR-L3 respectively have amino acid sequences of SEQ ID NOs: 37-39, and the CDR-H1, CDR-H2 and CDR-H3 respectively have amino acid sequences of SEQ ID NOs: 40-42. According to the preferred embodiments, the VL region comprises an amino acid sequence at least 85% identical to SEQ ID NO: 55, and the VH region comprises an amino acid sequence at least 85% identical to SEQ ID NO: 56. In some specific examples, the VL and VH regions of the recombinant antibody or the antibody fragment respectively comprise amino acid sequences 100% identical to SEQ ID NOs: 55 and 56.

Also disclosed herein is a kit for detecting the presence of SARS-CoV (e.g., SARS-CoV-2) in a biological sample. The present kit comprises a first recombinant antibody, a second recombinant antibody, and a container containing the first and second recombinant antibodies, in which the first and second recombinant antibody are independently selected from the recombinant antibodies as described in the first aspect of the present disclosure. According to certain embodiments, one of the first and second recombinant antibodies serves as a capture antibody, and the other of the first and second recombinant antibodies serves as a detection antibody for use in an detection technique, e.g., an enzyme-linked immunosorbent assay (ELISA), lateral flow immunoassay (LFIA), and western blotting (WB) assay.

According to some embodiments, the CDR-L1, CDR-L2, CDR-L3, CDR-H1, CDR-H2 and CDR-H3 of the first recombinant antibody respectively comprise amino acid sequences of SEQ ID NOs: 31-36, and the CDR-L1, CDR-L2, CDR-L3, CDR-H1, CDR-H2 and CDR-H3 of the second recombinant antibody respectively comprise amino acid sequences of SEQ ID NOs: 37-42. In certain exemplary embodiments, the VL and VH regions of the first recombinant antibody respectively comprise amino acid sequences at least 85% identical to SEQ ID NOs: 53 and 54, and the VL and VH regions of the second recombinant antibody respectively comprise amino acid sequences at least 85% identical to SEQ ID NOs: 55 and 56. In one specific example, the VL and VH regions of the first recombinant antibody respectively comprise amino acid sequences 100% identical to SEQ ID NOs: 53 and 54, and the VL and VH regions of the second recombinant antibody respectively comprise amino acid sequences 100% identical to SEQ ID NOs: 55 and 56.

Another aspect of the present disclosure is directed to a method of determining whether a subject is infected by SARS-CoV via a biological sample isolated from the subject. The method comprises the steps of, detecting the presence or absence of a nucleocapsid protein of the SARS-CoV in the biological sample by use of the recombinant antibody or the kit of the present disclosure, wherein the presence of the nucleocapsid protein indicates that the subject is infected by the SARS-CoV. According to some embodiments, the SARS-CoV is SARS-CoV-1 (NCBI Reference Sequence: NC_004718.3), i.e., the coronavirus causing a multicountry outbreak in 2002 to 2004. According to some embodiments, the SARS-CoV is SARS-CoV-2 (NCBI Reference Sequence: NC_045512.2), i.e., the coronavirus causing COVID-19 in late 2019.

Depending on desired purposes, the biological sample may be bronchoalveolar lavage fluid, sputum, nasal tissue, pharyngeal tissue, feces, or blood.

Based on the result, a skilled artisan or a clinical practitioner may administer to a subject in need thereof an appropriate treatment in time. Specifically, in the case when the nucleocapsid protein is present in the biological sample of a subject, then a supplemental oxygen and/or an effective amount of a treatment (e.g., interferon-alpha (IFN-α), chloroquine, chloroquine phosphate, arbidol, indinavir, saquinavir, lopinavir, carfilzomib, ritonavir, ribavirin, remdesivir, atazanavir, darunavir, tipranavir, fosamprenavir, enzaplatovir, presatovir, abacavir, bortezomib, elvitegravir, maribavir, raltegravir, montelukast, deoxyrhapontin, polydatin, chalcone, disulfiram, carmofur, shikonin, ebselen, tideglusib, 1-methylpropyl 2-imidazolyl disulfide (PX12), thiadiazolidine-8 (TDZD-8), cyclosporin A, cinanserin, or a combination thereof) is administered to the subject so as to alleviate and/or ameliorate the symptoms associated with the SARS-CoV infection.

The subject is a mammal; preferably, a human.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where:

FIG. 1A: The detection limit of the nucleocapsid protein of SARS-CoV-2 was elucidated by applying 2-fold serial diluted nucleocapsid protein expressed by HEK293 cell to the LFIA device. SARS-CoV-2-N: Nucleocapsid protein derived from SARS-CoV-2. OC43-N: Nucleocapsid protein derived from coronavirus HCoV-OC43. NL63-N: Nucleocapsid protein derived from coronavirus HCoV-NL63. FIG. 1B: The detection limit of the nucleocapsid protein of SARS-CoV-2 was elucidated by applying 2-fold serial diluted nucleocapsid protein expressed by SARS-CoV-2 virus-infected cells to the LFIA device. Vero-E6/Mock: Vero E6 cells without virus infection; serving as negative control in the study. Vero-E6/SARS-CoV-2: Vero E6 cells infected by SARS-CoV-2. Expi293/Mock: Expi293 cells without virus infection; serving as negative control in the study. Huh-7/Mock: Huh-7 cells without virus infection; serving as negative control in the study. Huh-7/229E: Huh-7 cells infected by HCoV-229E.

DETAILED DESCRIPTION OF THE INVENTION

Figure 1A:
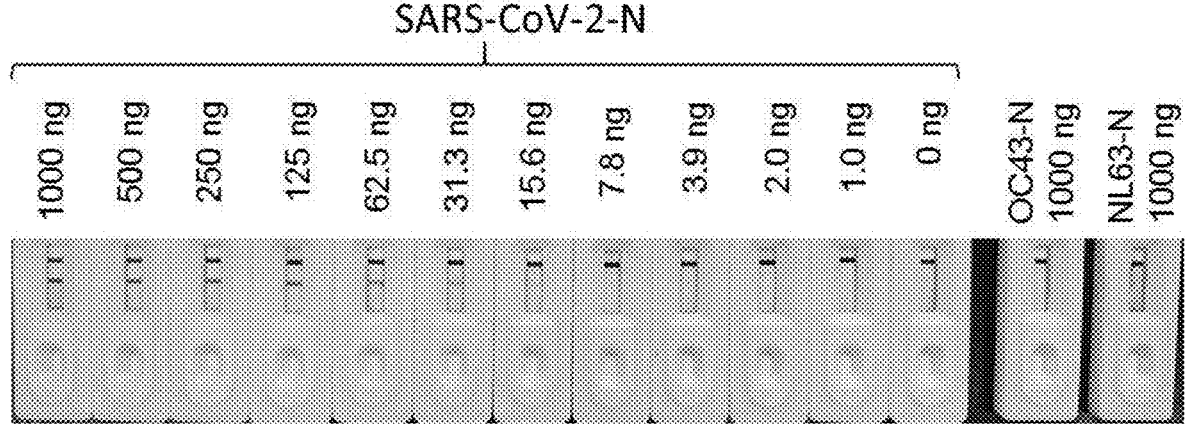
FIGS. 1A and 1B are photographs respectively depicting LFIA results and detection limits for the detection of the nucleocapsid protein of SARS-CoV-2 according to Example 3 of the present disclosure.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "antibody" is used in the broadest sense and specifically covers monoclonal antibodies (including full length monoclonal antibodies), polyclonal antibodies, multi-specific or multivalent antibodies (e.g., bi-specific antibodies), and antibody fragments so long as they exhibit the desired biological activity. The term "antibody fragment" or "the fragment of an antibody" refers to a portion of a full-length antibody, generally the antigen binding or variable region (i.e., VL and VH regions) of a full-length antibody. Examples of the antibody fragment include fragment antigen-binding (Fab), Fab', F(ab')2, single-chain variable fragment (scFv), diabody, linear antibody, single-chain antibody molecule, and multi-specific antibody formed from antibody fragments.

The term "$EC_{50}$" as used herein, refers to the concentration of an antibody or an antigen-binding portion thereof, which induces a response, either in an in vitro or an in vivo assay, which is 50% of the maximal response, i.e., halfway between the maximal response and the baseline.

The term "complementarity determining region (CDR)" used herein refers to the hypervariable region of an antibody molecule that forms a surface complementary to the 3-dimensional surface of a bound antigen. Proceeding from N-terminus to C-terminus, each of the antibody heavy and light chains comprises three CDRs (i.e., CDR-1, CDR-2, and CDR-3). A HLA-DR antigen-binding site, therefore, includes a total of six CDRs that comprise three CDRs from the variable region of a heavy chain (i.e., CDR-H1, CDR-H2, and CDR-H3), and three CDRs from the variable region of a light chain (i.e., CDR-L1, CDR-L2, and CDR-L3). The amino acid residues of CDRs are in close contact with bound antigen, wherein the closest antigen contact is usually associated with the heavy chain CDR3.

As used herein, the term "variable region" of an antibody refers to the amino-terminal regions of heavy or light chain of the antibody. These regions are generally the most variable parts of an antibody and contain the antigen-binding sites. The term "variable" refers to the fact that certain portions of the variable regions differ extensively in sequence among antibodies, and are used in the binding and specificity of each particular antibody for its particular antigen. However, the variability is not evenly distributed throughout the variable regions of antibodies. It is concentrated in three segments called complementarity-determining regions (CDRs) or hypervariable regions both in the light-chain and the heavy-chain variable regions. The more highly conserved portions of variable regions are called the framework (FR). The variable regions of native heavy and light chains each comprises four FR regions, largely adopting a beta-sheet configuration, connected by three CDRs, which form loops connecting, and in some cases forming part of, the beta-sheet structure. The CDRs in each chain are held together in close proximity by the FR regions, and with the CDRs from the other chain, contribute to the formation of the antigen-binding site of antibodies. The constant regions are not involved directly in binding an antibody to an antigen, but exhibit various effector functions, such as participation of the antibody in antibody-dependent cellular toxicity.

"Percentage (%) sequence identity" with respect to any amino acid sequence identified herein is defined as the percentage of amino acid residues in a candidate sequence that are identical with the amino acid residues in the specific reference sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNAS-TAR) software. Those skilled in the art can determine appropriate parameters for measuring alignment, including any algorithms needed to achieve maximal alignment over the full length of the sequences being compared. For purposes herein, sequence comparison between two amino acid sequences was carried out by computer program Blastp (protein-protein BLAST) provided online by Nation Center for Biotechnology Information (NCBI). The percentage sequence identity of a given sequence A to a subject sequence B (which can alternatively be phrased as a given sequence A that has a certain % sequence identity to a given sequence B) is calculated by the formula as follows:

$$\frac{X}{Y} \times 100\%$$

where X is the number of amino acid residues scored as identical matches by the sequence alignment program BLAST in that program's alignment of A and B, and where Y is the total number of amino acid residues in the subject sequence B.

As discussed herein, minor variations in the amino acid sequences of antibodies are contemplated as being encompassed by the presently disclosed and claimed inventive concept(s), providing that the variations in the amino acid sequence maintain at least 85% sequence identity, such as at least 85%, 86%, 87%, 88%, 89%, 90%, 91%, 92%, 93%, 94%, 95%, 96%, 97%, 98% and 99% sequence identity. Antibodies of the present disclosure may be modified specifically to alter a feature of the peptide unrelated to its physiological activity. For example, certain amino acids can be changed and/or deleted without affecting the physiological activity of the antibody in this study (i.e., the ability of binding to coronavirus). In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the peptide derivative. Fragments or analogs of antibodies can be readily prepared by those of ordinary skill in the art. Preferred amino- and carboxyl-termini of fragments or analogs occur near boundaries of functional regions.

The term "subject" refers to a mammal including the human species that can be subjected to the recombinant antibodies, kits and/or methods of the present invention. The term "subject" is intended to refer to both the male and female gender unless one gender is specifically indicated.

II. Description of the Invention (II-1) Methods for Selecting Coronavirus-Specific Antibody Fragments The first aspect of the present disclosure is directed to a method for selecting an antibody fragment specific to a coronavirus. According to embodiments of the present disclosure, the method comprises the steps of, (a) providing a phage-displayed single-chain variable fragment (scFv) library that comprises a plurality of phage-displayed scFvs, wherein the VH region of each phage-displayed scFvs has a binding affinity to protein A, and the VL region of each phage-displayed scFvs has a binding affinity to protein L;

(b) exposing the phage-displayed scFv library of the step (a) to a nucleocapsid protein derived from the coronavirus;

(c) selecting, from the phage-displayed scFv library of the step (b), a plurality of phages that respectively express scFvs exhibiting binding affinity to the nucleocapsid protein;

(d) respectively enabling the plurality of phages selected in the step (c) to express a plurality of soluble scFvs;

(e) exposing the plurality of soluble scFvs of the step (d) to the nucleocapsid protein;

(f) determining the respective binding affinity of the plurality of soluble scFvs to the nucleocapsid protein in the step (e); and (g) based on the results determined in the step (f), selecting one soluble scFv that exhibits superior affinity over the other soluble scFvs of the plurality of soluble scFvs as the antibody fragment.

The present method is useful in selecting an antibody fragment exhibiting a binding affinity and specificity to a coronavirus. According to some embodiments of the present disclosure, the coronavirus detectable by the selected antibody fragment is SARS-CoV-1. According to certain embodiments of the present disclosure, the coronavirus detectable by the selected antibody fragment is SARS-CoV-2.

In the step (a), a phage-displayed scFv library is provided. According to the embodiments of the present disclosure, the framework of the phage-displayed scFv library is based on the human IGKV1-NL1*01/IGHV3-23*04 germline sequence, and the complementarity determining region (CDR, including CDR-L1, CDR-L2, CDR-L3, CDR-H1, CDR-H2, and CDR-H3) thereof are diversified by PCR reaction using desired primers. After the selection of protein A and protein L, the phage-displayed scFv library (hereinafter as "GH2 library," including GH2-5, GH2-6, GH2-7, GH2-8, GH2-9, GH2-10, GH2-11, GH2-12, GH2-13, GH2-14, GH2-16, GH2-18, GH2-20, GH2-22, and GH2-24 libraries as illustrated in the examples of the present disclosure) is produced, in which each of the plurality of phage-displayed scFvs has a VH region capable of binding to protein A, and a VL region capable of binding to protein L. This phage-displayed scFv library can be constructed using the method described in the PCT applications, PCT/US2016/19128 and PCT/US18/56627, and the publication of Ing-Chien Chen et al. (High throughput discovery of influenza virus neutralizing antibodies from phage-displayed synthetic antibody libraries, *Scientific Reports* 7, Article number: 14455 (2017)). The entirety of the application and publication are incorporated herein by reference.

In the step (b), the GH2 library is exposed to a nucleocapsid protein derived from the coronavirus. According to some embodiments, the coronavirus is SARS-CoV-2; in these embodiments, the nucleocapsid protein comprises the amino acid sequence of SEQ ID NO: 58. According to certain embodiments, the nucleocapsid protein is immobilized on a matrix (such as an agarose resin or polyacrylamide) and then mixed with the present GH2 library.

In the step (c), a plurality of phages respectively expressing scFvs that exhibit binding affinity to the nucleocapsid protein are selected from the GH2 library. Specifically, the product of the step (b) is subjected to an elution buffer, which generally is an acidic solution (such as glycine solution, pH 2.2), so as to disrupt the binding between the nucleocapsid protein and phage-display scFv. By this way, the plurality of phages that respectively express scFvs exhibiting binding affinity to the nucleocapsid protein are collected.

Optionally, the step (c) is carried out under an acidic condition. Specifically, the product of the step (b) may be subjected to an acidic treatment (for example, a washing buffer having a pH value ranging between 5-7, such as pH 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9 or 7; preferably, a washing buffer having a pH value of 5.0) followed by the afore-mentioned elution step to collect the plurality of phages.

Next, in the step (d), the plurality of phages selected in the step (c) are subjected to conditions that enable them to produce a plurality of soluble scFvs. This step can be carried out by using methods known to any person having ordinary skill in the art. According to certain embodiments of the present disclosure, the expression of VH and VL regions may be driven by a lactose operon (lac operon); as known by one skilled artisan, the lac operon would be induced by isopropyl-thio-β-D-galactoside (IPTG), which then drives the expression of the down-stream genes (i.e., genes encoding the VH and VL regions). The produced scFv are then secreted into the supernatant of culture medium and could be collected therefrom.

In the step (e), the soluble scFvs produced in the step (d) are respectively mixed with the nucleocapsid protein so as to form the protein-scFv complexes.

Then, in the step (f), the level of the protein-scFv complexes formed in the step (e) is determined by a method known to a person having ordinary skill in the art for analyzing the binding affinity of two molecules (e.g., the binding affinity of an antibody to an antigen); for example, ELISA, WB assay, flow cytometry, or LFIA. In general, the level of the protein-scFv complexes is proportional to the binding affinity of the scFv to the nucleocapsid protein. According to one working example, the level of the protein-scFv complex (i.e., the binding affinity of the soluble scFv to the nucleocapsid protein) is determined by ELISA.

Finally, in the step (g), the antibody fragment is selected based on the binding affinity determined in the step (f). More specifically, the soluble scFv that exhibits superior affinity to the nucleocapsid protein over the other soluble scFvs of the plurality of soluble scFvs is selected as the antibody fragment.

(II-2) Methods for Producing Recombinant Antibodies

The antibody fragment selected by the method of Section (II-1) is useful in the preparation of a recombinant antibody, which structurally comprises a VL region, a light chain constant (CL) region, a VH region and a heavy chain constant (CH) region. The method of using the antibody fragment to produce the recombinant antibody comprises the steps of, (a) providing a phage that expresses the antibody fragment;

(b) extracting a phagemid DNA corresponding to the phage of the step (a);

(c) respectively amplifying a first nucleic acid sequence that encodes a VH region, and a second nucleic acid sequence that encodes a VL region by PCR using the phagemid DNA of the step (b) as a template;

(d) inserting the first and second nucleic acid sequences into an expression vector that comprises a third and a fourth nucleic acid sequences, wherein the third nucleic acid sequence encodes the CH region of an immunoglobulin, and the fourth nucleic acid sequence encodes the CL region of the immunoglobulin; and (e) transfecting a host cell with the expression vector of the step (d) that comprises the first, second, third, and fourth nucleic acid sequences so as to produce the recombinant antibody.

In the present method, the phage that expresses the antibody fragment is used as a starting material for the preparation of a recombinant antibody (i.e., step (a)).

Then, the phagemid DNA corresponding to the antibody fragment-expressing phage is extracted as described in step (b). Depending on intended purposes, the phagemid may be extracted by lysing the phage; alternatively, the phagemid may be obtained from a bacterial clone (i.e., the phagemid-containing bacterial clone). The extraction of phage DNA from the phage or bacterial clone could be achieved via any conventional DNA extraction technique; for example, the phenol/chloroform assay, and detergent (e.g., sodium dodecyl sulfate, TWEEN®-20, NP-40, and TRITON® X-100)/acetic acid assay.

In the step (c), the thus extracted phagemid DNA then serves as a template to respectively amplify the first nucleic acid sequence that encodes the CDR-H1, CDR-H2, and CDR-H3 by PCR using specific primers (forward primer: SEQ ID NO: 64; reverse primer: SEQ ID NO: 65), and the second nucleic acid sequence that encodes the CDR-L1, CDR-L2, and CDR-L3 by PCR using specific primers (forward primer: SEQ ID NO: 66; reverse primer: SEQ ID NO: 67).

In the step (d), the amplified first and second nucleic acid sequences are inserted into an expression vector, which comprises a third nucleic acid sequence encoding the constant regions of the heavy chain of an immunoglobulin, and a fourth nucleic acid sequence encoding the constant regions of the light chain of the immunoglobulin. As could be appreciated, the immunoglobulin can be any of IgG, IgA, IgD, IgE, and IgM. In one preferred embodiment of the present disclosure, the immunoglobulin is IgG. Specifically, the first and second nucleic acid sequences are first linked by a linker, which is amplified from pIgG vector by PCR. According to the embodiment of the present disclosure, the linker comprises in sequence: the CL region, a bovine growth hormone (BGH) polyadenylation (polyA) signal, a human CMV promoter, and a signal peptide of IgG heavy chain. For the presences of the complementary sequences between the 3'-end of second nucleic acid sequence and the 5'-end of linker, and the complementary sequences between the 3'-end of the linker and the 5'-end of the first nucleic acid sequence, the second nucleic acid sequence, the linker and the first nucleic acid sequence can be assembled in sequence via overlap extension polymerase chain reaction (OE-PCR). The assembled product is then inserted into the expression vector pIgG by use of the restriction enzymes. Structurally, the constructed expression vector comprises in sequence: a first human CMV promoter, a signal peptide of IgG light chain, the second nucleic acid sequence, the CL region, a first BGH-polyA signal, a second human CMV promoter, a signal peptide of IgG heavy chain, the first nucleic acid sequence, the CH region, and a second BGH-polyA signal, in which the second nucleic acid sequence and the CL region are driven by the first human CMV promoter so as to express the light chain of the recombinant antibody, and the first nucleic acid sequence and the CH region are driven by the second human CMV promoter to express the heavy chain of the recombinant antibody.

In step (e), the expression vector constructed in step (d) is transfected into a host cell so as to produce the present recombinant antibody. The commonly used host cell is a mammalian cell, such as a HEK293 cell. The transfection can be performed by any method familiar by one skilled artisan, including chemical-based method (e.g., calcium phosphate, liposome, and cationic polymer), non-chemical method (e.g., electroporation, cell squeezing, sonoporation, optical transfection, protoplast fusion, and hydrodynamic delivery), particle-based method (e.g. gene gun, magneto-fection, and impalefection), and viral method (e.g., adeno-viral vector, sindbis viral vector, and lentiviral vector). The thus-produced recombinant antibody is secreted into the supernatant of the culture medium, and can be purified therefrom by any purification method familiar by any skilled person; for example, the purification can be achieved by affinity binding with protein A or protein G.

(II-3) Recombinant Antibodies

According to some embodiments of the present disclosure, seven antibody fragments are selected by the method of Section (II-1), and accordingly, seven recombinant antibodies are produced therefrom. Thus, also disclosed herein are seven recombinant antibodies, respectively designated as "antibody #7", "antibody #11", "antibody #21", "antibody #22", "antibody #33", "antibody #36" and "antibody #48" in the present disclosure. In structure, each recombinant antibody comprises a VL region and a VH region, in which the VL region comprises CDR-L1, CDR-L2 and CDR-L3, and the VH region comprises CDR-H1, CDR-H2 and CDR-H3.

According to some embodiments, the CDR-L1, CDR-L2 and CDR-L3 of antibody #7 respectively have the amino acid sequences of SEQ ID NOs: 1-3 (i.e., respectively having the amino acid sequences 100% identical to SEQ ID NOs: 1-3), and the CDR-H1, CDR-H2 and CDR-H3 of antibody #7 respectively have the amino acid sequences of SEQ ID NOs: 4-6 (i.e., respectively having the amino acid sequences 100% identical to SEQ ID NOs: 4-6). According to some embodiments, the VH region of antibody #7 comprises an amino acid sequence at least 85% (e.g., 85%, 86%, 87%, 88%, 89%, 90%, 91%, 92%, 93%, 94%, 95%, 96%, 97%, 98%, 990 or 100%) identical to SEQ ID NO: 43: and the VL region of antibody #7 comprises an amino acid sequence at least 85% (e.g., 85%, 86%, 87%, 88%, 89%, 90%, 91%, 92%, 93%, 94%, 95%, 96%, 97%, 98%, 99% or 100%) identical to SEQ ID NO: 44. As would be appreciated, the sequence (e.g., the framework sequence) of the VH and VL regions may vary (e.g., being substituted by con-served or non-conserved amino acid residues) without affecting the binding affinity and/or specificity of the present antibody. Preferably, the sequence(s) of the VH and VL regions is/are conservatively substituted by one or more suitable amino acid(s) with similar properties; for example, the substitution of leucine (an nonpolar amino acid residue) by isoleucine, alanine, valine, proline, phenylalanine, or tryptophan (another nonpolar amino acid residue); the sub-stitution of aspartate (an acidic amino acid residue) by glutamate (another acidic amino acid residue); or the sub-stitution of lysine (an basic amino acid residue) by arginine or histidine (another basic amino acid residue). According to the preferred embodiments, the VL and VH regions of antibody #7 respectively comprise amino acid sequences at least 90,% identical to SEQ ID NOs: 43 and 44. More preferably, the VL and VH regions of antibody #7 respec-tively comprise the amino acid sequences at least 95% identical to SEQ ID NOs: 43 and 44. In one working example of the present disclosure, the VL region of antibody #7 has the amino acid sequence of SEQ ID NO: 43 (i.e., having an amino acid sequence 100% identical to SEQ ID NO: 43), and the VH region of antibody #7 has the amino acid sequence of SEQ ID NO: 44 (i.e., having an amino acid sequence 100% identical to SEQ ID NO: 44).

According to some embodiments, the CDR-L1, CDR-L2 and CDR-L3 of antibody #11 respectively have the amino acid sequences of SEQ ID NOs: 7-9, and the CDR-H1, CDR-H2 and CDR-H3 of antibody #11 respectively have the amino acid sequences of SEQ ID NOs: 10-12. According to some embodiments, the VH region of antibody #11 com-prises an amino acid sequence at least 85% identical to SEQ ID NO: 45; and the VL region of antibody #11 comprises an amino acid sequence at least 85% identical to SEQ ID NO: 46. According to the preferred embodiments, the VL and VH regions of antibody #11 respectively comprise the amino acid sequences at least 90% identical to SEQ ID NOs: 45 and 46. More preferably, the VL and VH regions of antibody #11 respectively comprise the amino acid sequences at least 95% identical to SEQ ID NOs: 45 and 46. In one working example of the present disclosure, the VL region of antibody #11 has the amino acid sequence of SEQ ID NO: 45, and the VH region of antibody #11 has the amino acid sequence of SEQ ID NO: 46.

According to some embodiments, the CDR-L1, CDR-L2 and CDR-L3 of antibody #21 respectively have the amino acid sequences of SEQ ID NOs: 13-15, and the CDR-H1, CDR-H2 and CDR-H3 of antibody #21 respectively have the amino acid sequences of SEQ ID NOs: 16-18. According to some embodiments, the VH region of antibody #21 comprises an amino acid sequence at least 85% identical to SEQ ID NO: 47 and the VL region of antibody #21 com-prises an amino acid sequence at least 85% identical to SEQ ID NO: 48. According to the preferred embodiments, the VL and VH regions of antibody #21 respectively comprise the amino acid sequences at least 90/o identical to SEQ ID NOs: 47 and 48. More preferably, the VL and VH regions of antibody #21 respectively comprise the amino acid sequences at least 95% identical to SEQ ID NOs: 47 and 48. In one working example of the present disclosure, the VL region of antibody #21 has the amino acid sequence of SEQ ID NO: 47, and the VH region of antibody #21 has the amino acid sequence of SEQ ID NO: 48.

According to certain embodiments, the CDR-L1, CDR-L2 and CDR-L3 of antibody #22 respectively have the amino acid sequences of SEQ ID NOs: 19-21, and the CDR-H1, CDR-H2 and CDR-H3 of antibody #22 respec-tively have the amino acid sequences of SEQ ID NOs: 22-24. According to some embodiments, the VH region of antibody #22 comprises an amino acid sequence at least 85% identical to SEQ ID NO: 49; and the VL region of antibody #22 comprises an amino acid sequence at least 85% identical to SEQ ID NO: 50. According to the preferred embodiments, the VL and VH regions of antibody #22 respectively comprise the amino acid sequences at least 90% identical to SEQ ID NOs: 49 and 50. More preferably, the VL and VH regions of antibody #22 respectively comprise the amino acid sequences at least 95% identical to SEQ ID NOs: 49 and 50. In one working example of the present disclosure, the VL region of antibody #22 has the amino acid sequence of SEQ ID NO: 49, and the VH region of antibody #22 has the amino acid sequence of SEQ ID NO: 50.

According to certain embodiments, the CDR-L1, CDR-L2 and CDR-L3 of antibody #33 respectively have the amino acid sequences of SEQ ID NOs: 25-27, and the CDR-H1, CDR-H2 and CDR-H3 of antibody #33 respectively have the amino acid sequences of SEQ ID NOs: 28-30. According to some embodiments, the VH region of antibody #33 comprises an amino acid sequence at least 85% identical to SEQ ID NO: 51; and the VL region of antibody #33 comprises an amino acid sequence at least 85% identical to SEQ ID NO: 52. According to the preferred embodiments, the VL and VH regions of antibody #33 respectively comprise the amino acid sequences at least 90% identical to SEQ ID NOs: 51 and 52. More preferably, the VL and VH regions of antibody #33 respectively comprise the amino acid sequences at least 95% identical to SEQ ID NOs: 51 and 52. In one working example of the present disclosure, the VL region of antibody #33 has the amino acid sequence of SEQ ID NO: 51, and the VH region of antibody #33 has the amino acid sequence of SEQ ID NO: 52.

According to some embodiments, the CDR-L1, CDR-L2 and CDR-L3 of antibody #36 respectively have the amino acid sequences of SEQ ID NOs: 31-33, and the CDR-H1, CDR-H2 and CDR-H3 of antibody #36 respectively have the amino acid sequences of SEQ ID NOs: 34-36. According to some embodiments, the VH region of antibody #36 comprises an amino acid sequence at least 85% identical to SEQ ID NO: 53; and the VL region of antibody #36 comprises an amino acid sequence at least 85% identical to SEQ ID NO: 54. According to the preferred embodiments, the VL and VH regions of antibody #36 respectively comprise the amino acid sequences at least 90% identical to SEQ ID NOs: 53 and 54. More preferably, the VL and VH regions of antibody #36 respectively comprise the amino acid sequences at least 95% identical to SEQ ID NOs: 53 and 54. In one working example of the present disclosure, the VL region of antibody #36 has the amino acid sequence of SEQ ID NO: 53, and the VH region of antibody #36 has the amino acid sequence of SEQ ID NO: 54.

According to some embodiment, the CDR-L1, CDR-L2 and CDR-L3 of antibody #48 respectively have the amino acid sequences of SEQ ID NOs: 37-39, and the CDR-H1, CDR-H2 and CDR-H3 of antibody #48 respectively have the amino acid sequences of SEQ ID NOs: 40-42. According to some embodiments, the VH region of antibody #48 comprises an amino acid sequence at least 85% identical to SEQ ID NO: 55, and the VL region of antibody #48 comprises an amino acid sequence at least 85% identical to SEQ ID NO: 56. According to the preferred embodiments, the VL and VH regions of antibody #48 respectively comprise the amino acid sequences at least 90% identical to SEQ ID NOs: 55 and 56. More preferably, the VL and VH regions of antibody #48 respectively comprise the amino acid sequences at least 95% identical to SEQ ID NOs: 55 and 56. In one working example of the present disclosure, the VL region of antibody #48 has the amino acid sequence of SEQ ID NO: 55, and the VH region of antibody #48 has the amino acid sequence of SEQ ID NO: 56.

According to some examples of the present disclosure, each of the seven antibodies (i.e., each of antibodies #7, #11, #21, #22, #33, #36 and #48) is useful in detecting SARS-CoV (e.g., SARS-CoV-2), and accordingly, may serve as a detecting agent for diagnosing SARS-CoV infection (e.g., SARS-CoV-2 infection).

(II-4) Kits for Detecting SARS-CoV

It is therefore another aspect of the present disclosure to provide a kit for the detection of SARS-CoV infection (e.g., SARS-CoV-2 infection). The kit includes, at least, a first recombinant antibody, a second recombinant antibody, and a container containing the first and second recombinant antibodies. According to certain embodiments of the present disclosure, the first and second recombinant antibodies are independently selected from the antibodies #7, #11, #21, #22, #33, #36 and #48 described above. The present kit is useful in detecting the SARS-CoV infection (e.g., SARS-CoV-2 infection) in a biological sample via any detection technique known to a skilled artisan, such as ELISA, LFIA, western blot assay, and flow cytometry. According to some working examples, one of the first and second recombinant antibodies serves as a detection antibody, and another of the first and second recombinant antibodies serves as a capture antibody for use in ELISA or LFIA.

In one embodiment, the kit comprises antibody #11 as the detection antibody, and antibody #33 as the capture antibody (designated as "antibody pair D11C33" in the present disclosure). In another embodiment, the kit comprises antibody #21 as the detection antibody, and antibody #11 as the capture antibody (designated as "antibody pair D21C11" in the present disclosure). In another embodiment, the kit comprises antibody #22 as the detection antibody, and antibody #36 as the capture antibody (designated as "antibody pair D22C36" in the present disclosure). In still another embodiment, the kit comprises antibody #33 as the detection antibody, and antibody #7 as the capture antibody (designated as "antibody pair D33C07" in the present disclosure). In further another embodiment, the kit comprises antibody #36 as the detection antibody, and antibody #48 as the capture antibody (designated as "antibody pair D36C48" in the present disclosure).

Optionally, the kit may further comprise a legend indicating how to use the antibody fragment or the recombinant antibody for detecting SARS-CoV infection (e.g., SARS-CoV-2 infection).

(II-5) Methods for Diagnosing SARS-CoV Infection

Also included herein is a method of determining whether a subject is infected by a SARS-CoV (e.g., SARS-CoV-2) via a biological sample isolated from the subject. The method comprises detecting the presence or absence of a nucleocapsid protein of the SARS-CoV (e.g., SARS-CoV-2) in the biological sample by use of the recombinant antibody or the kit of the present disclosure, wherein the presence of the nucleocapsid protein indicates that the subject is infected by the SARS-CoV (e.g., SARS-CoV-2), and the absence of the nucleocapsid protein indicates that the subject is not infect by the SARS-CoV (e.g., SARS-CoV-2).

According to some preferred embodiments, the coronavirus is SARS-CoV-2.

According to the preferred embodiments, the biological sample is obtained from the respiratory tract of the subject; preferably, the upper respiratory tract of the subject. Non-limiting examples of the biological sample suitable to be used in the present method include, a mucosa tissue, a fluid, or a secretion (e.g., sputum) isolated from the oral cavity, nasal cavity, trachea, bronchus, or lung of the subject.

Based on the diagnostic result, a skilled artisan or a clinical practitioner may administer to a subject need thereof (e.g., a subject suffering from SARS-CoV infection) a supplemental oxygen and/or an effective amount of a treatment thereby ameliorating and/or alleviating the symptom(s) associated with SARS-CoV infection. Examples of the treatment suitable to be used in the present method include, but are not limited to, IFN-α, chloroquine, chloroquine phosphate, arbidol, indinavir, saquinavir, lopinavir, carfilzomib, ritonavir, ribavirin, remdesivir, atazanavir, darunavir, tipranavir, fosamprenavir, enzaplatovir, presatovir, abacavir, bortezomib, elvitegravir, maribavir, raltegravir, montelukast, deoxyrhapontin, polydatin, chalcone, disulfiram, carmofur, shikonin, ebselen, tideglusib, 1-methylpropyl 2-imidazolyl disulfide (PX12), thiadiazolidine-8 (TDZD-8), cyclosporin A, cinanserin, and a combination thereof.

Alternatively, quarantine measures may be taken in time for a subject having SARS-CoV infection so as to prevent the possible spread of infection.

The subject that can be subjected to the present antibody, kit and/or method is a mammal, such as a human, a mouse, a rat, a monkey, a sheep, a goat, a cat, a dog, a horse, or a chimpanzee. Preferably, the subject is a human.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods

Preparation of Nucleocapsid Proteins

Seven genes encoding human coronavirus nucleocapsid proteins were derived from NCBI protein databank. These genes were codon optimized and synthesized for expression in *E. coli* and mammalian cells with pET15b and pcDNA3.1 vectors, respectively. These constructs were overexpressed in *E. coli* BL21 (DE3) cells with 0.5 mM IPTG induction at 16° C. The recombinant coronavirus nucleocapsid proteins were then purified using $Ni^{2+}$ charged column (for $His_6$-tag binding) with a binding buffer containing 50 mM Tris-HCl (pH 8.0) and 600 mM NaCl, and an elution buffer containing 50 mM Tris-HCl (pH 8.0), 600 mM NaCl and 500 mM imidazole by using chromatography system. Next, the fractions containing coronavirus nucleocapsid proteins were pooled for size exclusion separation with columns and elution buffer contains 50 mM Tris (pH 8.0) and 600 mM NaCl. These recombinant coronavirus nucleocapsid proteins contained RNA from *E. coli*, and the $A_{260}/A_{280}$ ratio was larger than 0.8. The concentration of recombinant coronavirus nucleocapsid proteins with protein assay was lower than optical detection with spectrophotometer and the extinction coefficient of each coronavirus nucleocapsid protein. Purified coronavirus nucleocapsid proteins were confirmed by sodium dodecyl sulfate polyacrylamide gel electrophoresis (SDS-PAGE). The constructs, including pcDNA3.1-SARS-CoV-2-N-His, pcDNA3.1-SARS-CoV-2-N-His, pcDNA3.1-OC43-N-His, pcDNA3.1-NL63-N-His and pcDNA3.1-229E-N-His were transfected into Expi-293 cells by transient transfection, and the $2\times10^8$ cells/100 ml and cultured for 48 hours. 10 ml of lysis buffer with inhibitors was added to the cells followed by the centrifuge at 12,000×g for 30 minutes at 4° C.

The thus-produced nucleocapsid proteins were designated as SARS-CoV-1-N protein, SARS-CoV-2-N protein, MERS-CoV-N protein, HCoV-OC43-N protein, HCoV-229E-N protein, HCoV-NL63-N protein, and HCoV- HKU1-N protein, which respectively comprised amino acid sequences of SEQ ID NOs: 57-63.

Cell Lines 293T (ATCC CRL-3216) was cultured in culture medium supplemented with 10% fetal bovine serum, penicillin-streptomycin (100×). Suspension EXPI293F™ cells were cultured in EXPI293™ expression medium at 37° C. with shaking 110 rpm in 8% $CO_2$ incubator. Vero E6 cells were cultured in culture medium with 2% FBS.

Viruses

Vero E6 cells were infected with SARS-CoV-2 (TCDC #4) at MOI 0.1 $TCID_{50}$ in culture medium with 2% FBS. At day-1, -2, and -3 post-infection, the infected cells and culture supernatant were collected for viral protein and RNA extraction by lysis buffer with proteinase inhibitor cocktail and RNA kit, respectively.

Characterization of the IgG1s Derived from the Selection and Screening Procedure with Phage-Displayed Synthetic scFv Libraries The construction and characterization of the phage-displayed synthetic scFv libraries followed the same procedure, without modification, as described in the PCT applications, PCT/US2016/19128 and PCT/US18/56627, and the publication of Ing-Chien Chen et al. (High throughput discovery of influenza virus neutralizing antibodies from phage-displayed synthetic antibody libraries, *Scientific Reports* 7, Article number: 14455 (2017)). The experimental procedures for panning the phage display libraries, selecting and screening of phage-displayed scFv binders, characterizing the scFvs binding to the cognate antigens and Protein A/L with ELISA, reformatting scFvs into IgG1s, expressing and purifying IgG1s, and determining $EC_{50}$ for the antibody-antigen interaction with ELISA have been described in the co-pending PCT applications, PCT/US2016/19128 and PCT/US18/56627.

Detection of Recombinant N Proteins with Sandwich ELISA

HRP was conjugated to detection antibody with HRP conjugation kit. 50 μg of purified IgG was added to HRP mix with molar ratio IgG:HRP=1:2, and the conjugation reaction was quenched according to manufacturer's instruction. Sandwich ELISAs were carried out with 96-well plate, which was coated with 1 μg of purified capture IgG for each well at 4° C. overnight. The recombinant nucleocapsid proteins were added to each well coated with capture antibody for one hour. After washing, 0.625 μg/ml HRP conjugated detection IgG (100 μL per well) was added to each well. The color was developed by adding substrate (100 μL per well) to each well for 5 minutes before adding 1 N HCl (100 μL per well) to stop the chromogenic reaction. The absorbance at 450 nm was measured. $EC_{50}$ of sandwich ELISA with pairing IgGs was also measured. One μg of purified capture IgG was coated for each well at 4° C. overnight. The recombinant nucleocapsid proteins were diluted by 2-fold serial dilution. 0.313 μg/mL of HRP conjugated detection IgG (100 μL per well) was added to each well. $EC_{50}$ was calculated.

Detection of Recombinant N Proteins with Sandwich Array

Antibody arrays were spotted on nitrocellulose membrane and conducted by sandwich detection protocol. Antibody samples were prepared in phosphate buffered saline (PBS) at the concentration of 1 mg/mL for arraying were sequential arrayed in a 10×10-dot array by gridding protocols with a float pin tools (96-pin tool with FSP3 pins with 100 nL slot). Each antibody was tandemly stamped in duplicate spots. The antibody arrays were blocked with 5% skim milk in PBST for 1 hour. The arrays are loaded with recombinant SARS-CoV-2 nucleocapsid protein, or SARS-CoV-2 nucleocapsid protein expressed 293F cell lysates after blocking. The concentration of recombinant SARS-CoV-2 nucleocapsid protein is six ug/mL. The concentration of total protein in cell lysates is 800 ug/mL, corresponds to 16 ug/mL of SARS-CoV-2 nucleocapsid protein. All arrays are incubated in the blocking buffer for 30 minutes, with rocking at 15 cycles per minute. After antigen loading, NC array was wash with PBST containing TWEEN® 20 (0.05%) twice to remove excess antigen. The antigen-loaded array was probed by incubation with IgG-HRP conjugate solution at 1000-fold dilution in blocking buffer for 30 minutes. After wash steps, the array was detected by incubation with 4-CN chromogenic substrate for 5 minutes. Spot densities on the array were quantitatively measured with imaging system and for statistical analysis.

Preparation of Colloidal Gold-Conjugated AL2C and IgGs

100 μl of 0.2 M $K_2CO_3$ (pH 11.5) was mixed with 10 ml colloidal gold solution (pH 5-6) to adjust pH (final pH 9), and then add 500 μl of IgG (1 mg/ml) or 50 μl of AL2C (3.35 mg/ml) to the colloidal gold solution for 40 minutes at room temperature. Add 1 ml of blocking buffer (10% BSA in 20 mM sodium borate, pH9.3) for 15 minutes at room temperature, followed by centrifugation (15,000 g, 30 minutes, 4° C.). The supernatant was discarded, and the pellet was completely resuspended in 10 ml wash buffer (1% BSA in 20 mM sodium borate, pH9.3), followed by centrifugation (15,000 g, 30 minutes, 4° C.). The washing procedure was repeated two times, and the pellet was resuspended in 1 ml 1% BSA in 20 mM sodium borate (pH9.3) for the procedure preparing the conjugate pad.

Assembly of the LFIA Strips

1 μg of the capture antibody, antigen or AL2C in PBS buffer were stripped on NP membrane per cm with lateral flow dispenser driven by syringe infusion pump. All other procedures for the preparation of the NC membrane with immobilized antigen or capture antibody, the preparation of the conjugate pad and the sample pad, and the preparation of the LFIA strip assembly were followed the protocol previously reported.

Example 1 Preparation and Characterization of Recombinant Antibodies

In order to develop antibodies as affinity reagents capable of characterizing SARS-CoV-2 nucleocapsid protein, a panel of nucleocapsid proteins was established from seven human coronaviruses, including SARS-CoV-2, SARS-CoV, MERS-CoV, HCoV-OC43, HCoV-229E, HCoV-NL63 and HCoV-HKU1. With these nucleocapsid proteins, a panel of anti-nucleocapsid protein antibodies was developed for use in sandwich ELISA and LFIA that were capable of detecting SARS-CoV-2 nucleocapsid protein without cross reactions to the nucleocapsid proteins from the other strains of human coronaviruses.

The antibodies specific to the nucleocapsid protein of SARS-CoV-2 were screened and selected by the procedure described in Materials and Methods of the present disclosure. Around 2,000 scFv candidates selected after the phage-displayed antibody library selection and screening were tested for binding to the target nucleocapsid proteins and compared with the negative control MERS-CoV nucleocapsid protein. Most of these scFv candidates bound to both nucleocapsid proteins of SARS-CoV-1 and SARS-CoV-2, while only a small fraction of the scFvs exhibited binding affinity to one of these two closely related nucleocapsid proteins (data not shown). None of the scFvs bound to the negative control, MERS-CoV nucleocapsid protein (data not shown). From these candidate scFvs, 150 scFvs were selected to be sequenced, and 120 scFvs sequences were non-redundant, in which 7 of the non-redundant sequences were further selected to be reformatted in human IgG1 framework, followed by being expressed in HEK293 expression system. The thus-obtained IgGs were respectively designated as antibody #7, antibody #11, antibody #21, antibody #22, antibody #33, antibody #36 and antibody #48. The VL and VH sequences of these antibody IgG1s were summarized in Table 1, and the binding affinity ($EC_{50}$) of these IgG1s to the nucleocapsid proteins in terms of measurements by ELISA were summarized in Table 2.

TABLE 1

VL and VH sequences of specified antibodies

| Name | Amino acid sequences* | SEQ ID NO |
|---|---|---|
| Antibody #7-VL | MADIQMTQSPSSLSASVGDRVTITCRASQDVEARVAWYQQKPGKAPKLLI FTSTRLYSGVPSRFSGSGSGTDFTLTISSLQPEDFATYYCQQIMPLPTTFGQ GTKVEIKR | 43 |
| Antibody #7-VH | EVQLVESGGGLVQPGGSLRLSCAASGFTIEDRWIHWVRQAPGKGLEWVA SIWPMEGLTRYADSVKGRFTISADTSKNTAYLQMNSLRAEDTAVYYCAR GYYGFDYWGQGTLVTVSSASAAA | 44 |
| Antibody #11-VL | MADIQMTQSPSSLSASVGDRVTITCRASQDVGGSVAWYQQKPGKAPKLLI SFPGGLYSGVPSRFSGSGSGTDFTLTISSLQPEDFATYYCQQYFSWPITFGQ GTKVEIKR | 45 |
| Antibody #11-VH | EVQLVESGGGLVQPGGSLRLSCAASGFTIQDRMIHWVRQAPGKGLEWVA SILPFLGATWYADSVKGRFTISADTSKNTAYLQMNSLRAEDTAVYYCARS WFSPFDYWGQGTLVTVSSASAAA | 46 |
| Antibody #21-VL | MADIQMTQSPSSLSASVGDRVTITCRASQDVGSNVAWYQQKPGKAPKLLI FSAPFLYSGVPSRFSGSGSGTDFTLTISSLQPEDFATYYCQQFYDWPLTFGQ GTKVEIKR | 47 |
| Antibody #21-VH | EVQLVESGGGLVQPGGSLRLSCAASGFTINNGSIHWVRQAPGKGLEWVA WIWPFGGYTYYADSVKGRFTISADTSKNTAYLQMNSLRAEDTAVYYCAR GSYGYDYWGQGTLVTVSSASAAA | 48 |

TABLE 1-continued

| VL and VH sequences of specified antibodies | | |
|---|---|---|
| Antibody<br>#22-VL | MADIQMTQSPSSLSASVGDRVTITCRASQDVDDNVAWYQQKPGKAPKLLI<br>SSSSGLYSGVPSRFSGSGSGTDFTLTISSLQPEDFATYYCQQSYNGPITFGQ<br>GTKVEIKR | 49 |
| Antibody<br>#22-VH | EVQLVESGGGLVQPGGSLRLSCAASGFTISSGSIHWVRQAPGKGLEWVASI<br>WPFGGYTSYADSVKGRFTISADTSKNTAYLQMNSLRAEDTAVYYCARGS<br>FGSDYWGQGTLVTVSSASAAA | 50 |
| Antibody<br>#33-VL | MADIQMTQSPSSLSASVGDRVTITCRASQDVYSSVAWYQQKPGKAPKLLIF<br>GSSFLYSGVPSRFSGSGSGTDFTLTISSLQPEDFATYYCQQYYDWPITFCQG<br>TKVEIKR | 51 |
| Antibody<br>#33-VH | EVQLVESGGGLVQPGGSLRLSCAASGFTINNGGIHWVRQAPGKGLEWVA<br>GIWPFWGSTSYADSVKGRFTISADTSKNTAYLQMNSLRAEDTAVYYCAR<br>GSYGFDYWGQGTLVTVSSASAAA | 52 |

*The CDR sequences were marked in boldface and underlined, including three CDRs
(i.e., CDR-L1, CDR-L2 and CDR-L3, from N-terminus to C-terminus, in sequence) in
the VL region, and three CDRs (i.e., CDR-H1, CDR-H2 and CDR-H3, from N-terminus to
C-terminus, in sequence) in the VH region.

| Name | Amino acid sequences* (from N-terminus to C-terminus) | SEQ ID NO |
|---|---|---|
| Antibody<br>#36-VL | MADIQMTQSPSSLSASVGDRVTITCRASQDVTTTVAWYQQKPGKAPKLLI<br>NKGSWLYSGVPSRFSGSGSGTDFTLTISSLQPEDFATYYCQQYNKWPLTF<br>GQGTKVEIKR | 53 |
| Antibody<br>#36-VH | EVQLVESGGGLVQPGGSLRLSCAASGFTINRYSIHWVRQAPGKGLEWVA<br>GTWPFGGDTTYADSVKGRFTISADTSKNTAYLQMNSLRAEDTAVYYCAR<br>GATSHDYWGQGTLVTVSSASAAA | 54 |
| Antibody<br>#48-VL | MADIQMTQSPSSLSASVGDRVTITCSGSSSNIGDNNVYWYQQKPGKAPKLL<br>IFGPAYLYSGVPSRFSGSGSGTDFTLTISSLQPEDFATYYCAAGYSDNNGIT<br>FGQGTKVEIKR | 55 |
| Antibody<br>#48-VH | EVQLVESGGGLVQPGGSLRLSCAASGFTISNFGIHWVRQAPGKGLEWVAG<br>TWPYSGYTFYADSVKGRFTISADTSKNTAYLQMNSLRAEDTAVYYCARF<br>DSYSYSGYMDYWGQGTLVTVSSASAAA | 56 |

*The CDR sequences were marked in boldface and underlined, including three CDRs
(i.e., CDR-L1, CDR-L2 and CDR-L3, from N-terminus to C-terminus, in sequence) in
the VL region, and three CDRs (i.e., CDR-H1, CDR-H2 and CDR-H3, from N-terminus to
C-terminus, in sequence) in the VH region.

TABLE 2

ELISA EC$_{50}$ of IgG candidates against recombinant proteins,
including SARS-CoV-2-N, SARS-CoV-N, MERS-CoV-N, NL63-
CoV-N, OC43-CoV-N, 229E-CoV-N, and HKU1-CoV-N.

| Target\EC$_{50}$<br>(ng/ml) | #7 | #11 | #21 | #22 | #33 | #36 | #48 |
|---|---|---|---|---|---|---|---|
| SARS-CoV-2 N | 3.7 | 7.6 | 18.0 | 4.4 | 1.4 | 0.8 | 46.7 |
| SARS-CoV N | 3.7 | 6.9 | 21.4 | 3.9 | 1.6 | 2.0 | 18.6 |
| MERS-CoV N | >2000 | >2000 | >2000 | >2000 | >2000 | >2000 | >2000 |
| NL63-CoV N | >2000 | >2000 | >2000 | >2000 | >2000 | >2000 | >2000 |
| OC43-CoV N | >2000 | >2000 | >2000 | >2000 | >2000 | >2000 | >2000 |
| 229E-CoV N | >2000 | >2000 | >2000 | >2000 | >2000 | >2000 | >2000 |
| HKU1-CoV N | >2000 | >2000 | >2000 | >2000 | >2000 | >2000 | >2000 |

65

The data of Table 2 demonstrated that each antibody of the present study exhibited a binding affinity and specificity to SARS-CoV, and accordingly provides a means to detect SARS-CoV infection (e.g., SARS-CoV-2 infection).

Example 2 Binding Affinity of Recombinant
Antibodies in Sandwich ELISA

The binding affinities of antibodies #7, #11, #21, #22, #33, #36 and #48 to the nucleocapsid protein of SARS-CoV-2 were examined by sandwich ELISA. As the data summarized in Table 3, the present antibodies were useful in serving as the detection and capture antibodies for detecting SARS-CoV-2, in which the $EC_{50}$ of antibody pair D21C11 against SARS-CoV-2 was 54.41 ng/ml, while the $EC_{50}$ of antibody pairs D11C33, D22C36, D33C07 and D36C48 against SARS-CoV-2 was lower than 30 ng/ml.

TABLE 3

Sandwich ELISA $EC_{50}$ of specified antibodies against
the nucleocapsid protein of SARS-CoV-2

| Antibody pair | $EC_{50}$ (ng/ml) | Note |
|---|---|---|
| D11C33 | 25.53 | Detection antibody: antibody #11 Capture antibody: antibody #33 |
| D21C11 | 54.41 | Detection antibody: antibody #21 Capture antibody: antibody #11 |
| D22C36 | 28.82 | Detection antibody: antibody #22 Capture antibody: antibody #36 |
| D33C07 | 18.02 | Detection antibody: antibody #33 Capture antibody: antibody #7 |
| D36C48 | 20.66 | Detection antibody: antibody #36 Capture antibody: antibody #48 |

Example 3 Establishing a LFIA Device for Rapid
Test of the Nucleocapsid Protein of SARS-CoV-2

Figure 1B:
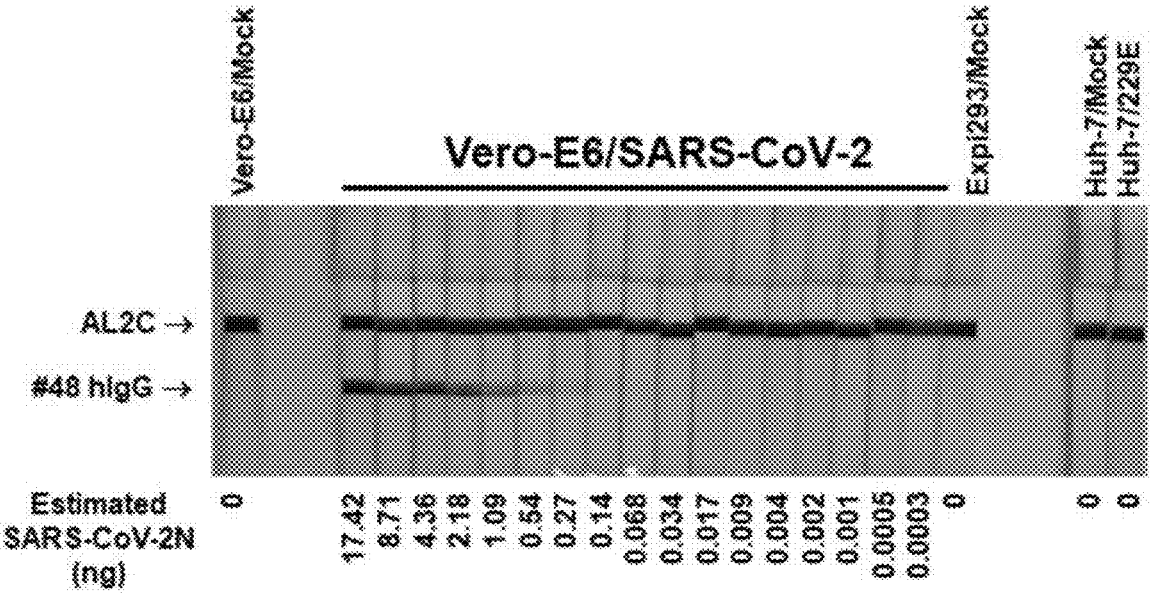

The antibody pair D36C48 was further used to construct a LFIA device. This IgG1 pair was selected because the expression quality and yields (data not shown) of both IgG1s were suitable for large scale manufacturing, and the conjugation efficiency of IgG1 #36 to colloidal gold was outstanding between pH7.5 and pH9.0. The prototype of the LFIA device was constructed with antibody #48 as the capture antibody and antibody #36 as the colloidal gold-conjugated detection antibody. The detection limit of the LFIA prototype was determined with two samples containing the nucleocapsid protein of SARS-CoV-2. The first sample contained the nucleocapsid protein derived from SARS-CoV-2, HCoV-OC43 or HCoV-NL63, which was expressed in HEK293 cell, and the cultured cells were lysed in the mixture of cell lysate containing 1× protein lysis buffer and 50% of total cellular proteins (FIG. 1A). According to the data of FIG. 1A, the antibody pair D36C48 exhibited binding specificity to the nucleocapsid protein of SARS-CoV-2, and the detection limit for SARS-CoV-2 was about 7.8 ng. The second sample contained SARS-CoV-2-infected Vero E6 cells, which were lysed with protein lysis buffer in the presence of 50% of total cellular proteins (FIG. 1B). The samples of the instant study were mimics to the complex mixture of nasal swab in the presence of lysis buffer to release the nucleocapsid protein in the intact viruses and infected cells. The detection limits for both samples are in the range of 0.1 ng/test.

In summary, seven antibodies, including antibodies #7, #11, #21, #22, #33, #36 and #48, selected from the GH synthetic antibody libraries were demonstrated to be capable of binding to the nucleocapsid protein of SARS-CoV-2 with high affinities and functional specificities. The optimal affinities of the selected antibodies for their corresponding nucleocapsid proteins were below 1 nM in $EC_{50}$ without the need for affinity maturation. The antibodies derived from the GH synthetic antibody libraries without further affinity maturation were used in sandwich ELISA and LFIA to detect the corresponding nucleocapsid proteins from lysed virus-infected cells with detection limit of 0.1 ng/test in highly complex specimen. The detection limit is close to the general acceptable detection limit for coronavirus detection with RIDTs. The present study demonstrated the feasibility of a general procedure in developing diagnostic antibodies that would be unavailable from animal-based antibody technologies.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A kit for detecting severe acute respiratory syndrome coronavirus (SARS-CoV), comprising a first recombinant antibody and a second recombinant antibody; and a container containing the first and second recombinant antibodies; wherein the VL region of the first recombinant antibody comprises an amino acid sequence 100% identical to SEQ ID NO: 53, and the VH region of the first recombinant antibody comprises an amino acid sequence 100% identical to SEQ ID NO: 54; and the VL region of the second recombinant antibody comprises an amino acid sequence at least 85% identical to SEQ ID NO: 55, and the VH region of the second recombinant antibody comprises an amino acid sequence 100% identical to SEQ ID NO: 56.

2. The kit of claim 1, wherein the SARS-CoV is SARS-CoV-1.

3. The kit of claim 1, wherein the SARS-CoV is SARS-CoV-2.

4. A method of determining whether a subject is infected by severe acute respiratory syndrome coronavirus (SARS-CoV) comprising:

mixing a biological sample isolated from the subject with a first recombinant antibody and a second recombinant antibody, wherein the VL region of the first recombinant antibody comprises an amino acid sequence 100% identical to SEQ ID NO: 53, and the VH region of the first recombinant antibody comprises an amino acid sequence 100% identical to SEQ ID NO: 54; and the VL region of the second recombinant antibody comprises an amino acid sequence 100% identical to SEQ ID NO: 55, and the VH region of the second recombinant antibody comprises an amino acid sequence 100% identical to SEQ ID NO: 56; and detecting the presence or absence of a nucleocapsid protein of the SARS-CoV bound to the first or second recombinant antibody in the biological sample, wherein the presence of the nucleocapsid protein indicates that the subject is infected by the SARS-CoV.

5. The method of claim 4, wherein the coronavirus is SARS-CoV-1.

6. The method of claim 4, wherein the coronavirus is SARS-CoV-2.

7. The method of claim 4, wherein the biological sample is bronchoalveolar lavage fluid, sputum, nasal tissue, pharyngeal tissue, feces, or blood.

8. The method of claim 4, wherein the subject is a human.

* * * * *

SEQUENCE LISTING

```
<160> NUMBER OF SEQ ID NOS: 67

<210> SEQ ID NO 1
<211> LENGTH: 11
<212> TYPE: PRT
<213> ORGANISM: Artificial Sequence
<220> FEATURE:
<223> OTHER INFORMATION: synthesized_#7_CDRL1

<400> SEQUENCE: 1

Arg Ala Ser Gln Asp Val Glu Ala Arg Val Ala
1               5                   10

<210> SEQ ID NO 2
<211> LENGTH: 8
<212> TYPE: PRT
<213> ORGANISM: Artificial Sequence
<220> FEATURE:
<223> OTHER INFORMATION: synthesized_#7_CDRL2
```

<400> SEQUENCE: 2

Phe Thr Ser Thr Arg Leu Tyr Ser
1               5

<210> SEQ ID NO 3
<211> LENGTH: 9
<212> TYPE: PRT
<213> ORGANISM: Artificial Sequence
<220> FEATURE:
<223> OTHER INFORMATION: synthesized_#7_CDRL3

<400> SEQUENCE: 3

Gln Gln Ile Met Pro Leu Pro Thr Thr
1               5

<210> SEQ ID NO 4
<211> LENGTH: 13
<212> TYPE: PRT
<213> ORGANISM: Artificial Sequence
<220> FEATURE:
<223> OTHER INFORMATION: synthesized_#7_CDRH1

<400> SEQUENCE: 4

Ala Ala Ser Gly Phe Thr Ile Glu Asp Arg Trp Ile His
1               5                   10

<210> SEQ ID NO 5
<211> LENGTH: 10
<212> TYPE: PRT
<213> ORGANISM: Artificial Sequence
<220> FEATURE:
<223> OTHER INFORMATION: synthesized_#7_CDRH2

<400> SEQUENCE: 5

Ser Ile Trp Pro Met Glu Gly Leu Thr Arg
1               5                   10

<210> SEQ ID NO 6
<211> LENGTH: 9
<212> TYPE: PRT
<213> ORGANISM: Artificial Sequence
<220> FEATURE:
<223> OTHER INFORMATION: synthesized_#7_CDRH3

<400> SEQUENCE: 6

Ala Arg Gly Tyr Tyr Gly Phe Asp Tyr
1               5

<210> SEQ ID NO 7
<211> LENGTH: 11
<212> TYPE: PRT
<213> ORGANISM: Artificial Sequence
<220> FEATURE:
<223> OTHER INFORMATION: synthesized_#11_CDRL1

<400> SEQUENCE: 7

Arg Ala Ser Gln Asp Val Gly Gly Ser Val Ala
1               5                   10

<210> SEQ ID NO 8
<211> LENGTH: 8
<212> TYPE: PRT
<213> ORGANISM: Artificial Sequence
<220> FEATURE:
<223> OTHER INFORMATION: synthesized_#11_CDRL2

```
<400> SEQUENCE: 8

Ser Phe Pro Gly Gly Leu Tyr Ser
1               5

<210> SEQ ID NO 9
<211> LENGTH: 9
<212> TYPE: PRT
<213> ORGANISM: Artificial Sequence
<220> FEATURE:
<223> OTHER INFORMATION: synthesized_#11_CDRL3

<400> SEQUENCE: 9

Gln Gln Tyr Phe Ser Trp Pro Ile Thr
1               5

<210> SEQ ID NO 10
<211> LENGTH: 13
<212> TYPE: PRT
<213> ORGANISM: Artificial Sequence
<220> FEATURE:
<223> OTHER INFORMATION: synthesized_#11_CDRH1

<400> SEQUENCE: 10

Ala Ala Ser Gly Phe Thr Ile Gln Asp Arg Met Ile His
1               5                   10

<210> SEQ ID NO 11
<211> LENGTH: 10
<212> TYPE: PRT
<213> ORGANISM: Artificial Sequence
<220> FEATURE:
<223> OTHER INFORMATION: synthesized_#11_CDRH2

<400> SEQUENCE: 11

Ser Ile Leu Pro Phe Leu Gly Ala Thr Trp
1               5                   10

<210> SEQ ID NO 12
<211> LENGTH: 10
<212> TYPE: PRT
<213> ORGANISM: Artificial Sequence
<220> FEATURE:
<223> OTHER INFORMATION: synthesized_#11_CDRH3

<400> SEQUENCE: 12

Ala Arg Ser Trp Phe Ser Pro Phe Asp Tyr
1               5                   10

<210> SEQ ID NO 13
<211> LENGTH: 11
<212> TYPE: PRT
<213> ORGANISM: Artificial Sequence
<220> FEATURE:
<223> OTHER INFORMATION: synthesized_#21_CDRL1

<400> SEQUENCE: 13

Arg Ala Ser Gln Asp Val Gly Ser Asn Val Ala
1               5                   10

<210> SEQ ID NO 14
<211> LENGTH: 8
<212> TYPE: PRT
<213> ORGANISM: Artificial Sequence
<220> FEATURE:
<223> OTHER INFORMATION: synthesized_#21_CDRL2

<400> SEQUENCE: 14
```

```
Phe Ser Ala Pro Phe Leu Tyr Ser
1               5

<210> SEQ ID NO 15
<211> LENGTH: 9
<212> TYPE: PRT
<213> ORGANISM: Artificial Sequence
<220> FEATURE:
<223> OTHER INFORMATION: synthesized_#21_CDRL3

<400> SEQUENCE: 15

Gln Gln Phe Tyr Asp Trp Pro Leu Thr
1               5

<210> SEQ ID NO 16
<211> LENGTH: 13
<212> TYPE: PRT
<213> ORGANISM: Artificial Sequence
<220> FEATURE:
<223> OTHER INFORMATION: synthesized_#21_CDRH1

<400> SEQUENCE: 16

Ala Ala Ser Gly Phe Thr Ile Asn Asn Gly Ser Ile His
1               5                   10

<210> SEQ ID NO 17
<211> LENGTH: 10
<212> TYPE: PRT
<213> ORGANISM: Artificial Sequence
<220> FEATURE:
<223> OTHER INFORMATION: synthesized_#21_CDRH2

<400> SEQUENCE: 17

Trp Ile Trp Pro Phe Gly Gly Tyr Thr Tyr
1               5                   10

<210> SEQ ID NO 18
<211> LENGTH: 9
<212> TYPE: PRT
<213> ORGANISM: Artificial Sequence
<220> FEATURE:
<223> OTHER INFORMATION: synthesized_#21_CDRH3

<400> SEQUENCE: 18

Ala Arg Gly Ser Tyr Gly Tyr Asp Tyr
1               5

<210> SEQ ID NO 19
<211> LENGTH: 11
<212> TYPE: PRT
<213> ORGANISM: Artificial Sequence
<220> FEATURE:
<223> OTHER INFORMATION: synthesized_#22_CDRL1

<400> SEQUENCE: 19

Arg Ala Ser Gln Asp Val Asp Asp Asn Val Ala
1               5                   10

<210> SEQ ID NO 20
<211> LENGTH: 8
<212> TYPE: PRT
<213> ORGANISM: Artificial Sequence
<220> FEATURE:
<223> OTHER INFORMATION: synthesized_#22_CDRL2

<400> SEQUENCE: 20
```

```
Ser Ser Ser Ser Gly Leu Tyr Ser
1               5

<210> SEQ ID NO 21
<211> LENGTH: 9
<212> TYPE: PRT
<213> ORGANISM: Artificial Sequence
<220> FEATURE:
<223> OTHER INFORMATION: synthesized_#22_CDRL3

<400> SEQUENCE: 21

Gln Gln Ser Tyr Asn Gly Pro Ile Thr
1               5

<210> SEQ ID NO 22
<211> LENGTH: 13
<212> TYPE: PRT
<213> ORGANISM: Artificial Sequence
<220> FEATURE:
<223> OTHER INFORMATION: synthesized_#22_CDRH1

<400> SEQUENCE: 22

Ala Ala Ser Gly Phe Thr Ile Ser Ser Gly Ser Ile His
1               5                   10

<210> SEQ ID NO 23
<211> LENGTH: 10
<212> TYPE: PRT
<213> ORGANISM: Artificial Sequence
<220> FEATURE:
<223> OTHER INFORMATION: synthesized_#22_CDRH2

<400> SEQUENCE: 23

Ser Ile Trp Pro Phe Gly Gly Tyr Thr Ser
1               5                   10

<210> SEQ ID NO 24
<211> LENGTH: 9
<212> TYPE: PRT
<213> ORGANISM: Artificial Sequence
<220> FEATURE:
<223> OTHER INFORMATION: synthesized_#22_CDRH3

<400> SEQUENCE: 24

Ala Arg Gly Ser Phe Gly Ser Asp Tyr
1               5

<210> SEQ ID NO 25
<211> LENGTH: 11
<212> TYPE: PRT
<213> ORGANISM: Artificial Sequence
<220> FEATURE:
<223> OTHER INFORMATION: synthesized_#33_CDRL1

<400> SEQUENCE: 25

Arg Ala Ser Gln Asp Val Tyr Ser Ser Val Ala
1               5                   10

<210> SEQ ID NO 26
<211> LENGTH: 8
<212> TYPE: PRT
<213> ORGANISM: Artificial Sequence
<220> FEATURE:
<223> OTHER INFORMATION: synthesized_#33_CDRL2

<400> SEQUENCE: 26

Phe Gly Ser Ser Phe Leu Tyr Ser
```

-continued

```
1               5

<210> SEQ ID NO 27
<211> LENGTH: 8
<212> TYPE: PRT
<213> ORGANISM: Artificial Sequence
<220> FEATURE:
<223> OTHER INFORMATION: synthesized_#33_CDRL3

<400> SEQUENCE: 27

Gln Gln Tyr Tyr Asp Trp Pro Ile
1               5

<210> SEQ ID NO 28
<211> LENGTH: 13
<212> TYPE: PRT
<213> ORGANISM: Artificial Sequence
<220> FEATURE:
<223> OTHER INFORMATION: synthesized_#33_CDRH1

<400> SEQUENCE: 28

Ala Ala Ser Gly Phe Thr Ile Asn Asn Gly Gly Ile His
1               5                   10

<210> SEQ ID NO 29
<211> LENGTH: 10
<212> TYPE: PRT
<213> ORGANISM: Artificial Sequence
<220> FEATURE:
<223> OTHER INFORMATION: synthesized_#33_CDRH2

<400> SEQUENCE: 29

Gly Ile Trp Pro Phe Trp Gly Ser Thr Ser
1               5                   10

<210> SEQ ID NO 30
<211> LENGTH: 9
<212> TYPE: PRT
<213> ORGANISM: Artificial Sequence
<220> FEATURE:
<223> OTHER INFORMATION: synthesized_#33_CDRH3

<400> SEQUENCE: 30

Ala Arg Gly Ser Tyr Gly Phe Asp Tyr
1               5

<210> SEQ ID NO 31
<211> LENGTH: 11
<212> TYPE: PRT
<213> ORGANISM: Artificial Sequence
<220> FEATURE:
<223> OTHER INFORMATION: synthesized_#36_CDRL1

<400> SEQUENCE: 31

Arg Ala Ser Gln Asp Val Thr Thr Thr Val Ala
1               5                   10

<210> SEQ ID NO 32
<211> LENGTH: 8
<212> TYPE: PRT
<213> ORGANISM: Artificial Sequence
<220> FEATURE:
<223> OTHER INFORMATION: synthesized_#36_CDRL2

<400> SEQUENCE: 32

Asn Lys Gly Ser Trp Leu Tyr Ser
1               5
```

```
<210> SEQ ID NO 33
<211> LENGTH: 9
<212> TYPE: PRT
<213> ORGANISM: Artificial Sequence
<220> FEATURE:
<223> OTHER INFORMATION: synthesized_#36_CDRL3

<400> SEQUENCE: 33

Gln Gln Tyr Asn Lys Trp Pro Leu Thr
1               5

<210> SEQ ID NO 34
<211> LENGTH: 13
<212> TYPE: PRT
<213> ORGANISM: Artificial Sequence
<220> FEATURE:
<223> OTHER INFORMATION: synthesized_#36_CDRH1

<400> SEQUENCE: 34

Ala Ala Ser Gly Phe Thr Ile Asn Arg Tyr Ser Ile His
1               5                   10

<210> SEQ ID NO 35
<211> LENGTH: 10
<212> TYPE: PRT
<213> ORGANISM: Artificial Sequence
<220> FEATURE:
<223> OTHER INFORMATION: synthesized_#36_CDRH2

<400> SEQUENCE: 35

Gly Ile Trp Pro Phe Gly Gly Asp Thr Thr
1               5                   10

<210> SEQ ID NO 36
<211> LENGTH: 9
<212> TYPE: PRT
<213> ORGANISM: Artificial Sequence
<220> FEATURE:
<223> OTHER INFORMATION: synthesized_#36_CDRH3

<400> SEQUENCE: 36

Ala Arg Gly Ala Thr Ser His Asp Tyr
1               5

<210> SEQ ID NO 37
<211> LENGTH: 13
<212> TYPE: PRT
<213> ORGANISM: Artificial Sequence
<220> FEATURE:
<223> OTHER INFORMATION: synthesized_#48_CDRL1

<400> SEQUENCE: 37

Ser Gly Ser Ser Ser Asn Ile Gly Asp Asn Asn Val Tyr
1               5                   10

<210> SEQ ID NO 38
<211> LENGTH: 8
<212> TYPE: PRT
<213> ORGANISM: Artificial Sequence
<220> FEATURE:
<223> OTHER INFORMATION: synthesized_#48_CDRL2

<400> SEQUENCE: 38

Phe Gly Pro Ala Tyr Leu Tyr Ser
1               5
```

```
<210> SEQ ID NO 39
<211> LENGTH: 11
<212> TYPE: PRT
<213> ORGANISM: Artificial Sequence
<220> FEATURE:
<223> OTHER INFORMATION: synthesized_#48_CDRL3

<400> SEQUENCE: 39

Ala Ala Gly Tyr Ser Asp Asn Asn Gly Ile Thr
1               5                   10

<210> SEQ ID NO 40
<211> LENGTH: 13
<212> TYPE: PRT
<213> ORGANISM: Artificial Sequence
<220> FEATURE:
<223> OTHER INFORMATION: synthesized_#48_CDRH1

<400> SEQUENCE: 40

Ala Ala Ser Gly Phe Thr Ile Ser Asn Phe Gly Ile His
1               5                   10

<210> SEQ ID NO 41
<211> LENGTH: 10
<212> TYPE: PRT
<213> ORGANISM: Artificial Sequence
<220> FEATURE:
<223> OTHER INFORMATION: synthesized_#48_CDRH2

<400> SEQUENCE: 41

Gly Ile Trp Pro Tyr Gly Gly Tyr Thr Phe
1               5                   10

<210> SEQ ID NO 42
<211> LENGTH: 14
<212> TYPE: PRT
<213> ORGANISM: Artificial Sequence
<220> FEATURE:
<223> OTHER INFORMATION: synthesized_#48_CDRH3

<400> SEQUENCE: 42

Ala Arg Phe Asp Ser Tyr Ser Tyr Ser Gly Tyr Met Asp Tyr
1               5                   10

<210> SEQ ID NO 43
<211> LENGTH: 110
<212> TYPE: PRT
<213> ORGANISM: Artificial Sequence
<220> FEATURE:
<223> OTHER INFORMATION: synthesized_#7_VL

<400> SEQUENCE: 43

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Glu
            20                  25                  30

Ala Arg Val Ala Trp Tyr Gln Gln Lys Pro Gly Lys Ala Pro Lys Leu
        35                  40                  45

Leu Ile Phe Thr Ser Thr Arg Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ile Met Pro Leu
                85                  90                  95
```

Pro Thr Thr Phe Gly Gln Gly Thr Lys Val Glu Ile Lys Arg
            100                 105                 110

<210> SEQ ID NO 44
<211> LENGTH: 121
<212> TYPE: PRT
<213> ORGANISM: Artificial Sequence
<220> FEATURE:
<223> OTHER INFORMATION: synthesized_#7_VH

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Glu Asp Arg
            20                  25                  30

Trp Ile His Trp Val Arg Gln Ala Pro Gly Lys Gly Leu Glu Trp Val
        35                  40                  45

Ala Ser Ile Trp Pro Met Glu Gly Leu Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Gly Phe Asp Tyr Trp Gly Gln Gly Thr Leu Val
            100                 105                 110

Thr Val Ser Ser Ala Ser Ala Ala Ala
        115                 120

<210> SEQ ID NO 45
<211> LENGTH: 110
<212> TYPE: PRT
<213> ORGANISM: Artificial Sequence
<220> FEATURE:
<223> OTHER INFORMATION: synthesized_#11_VL

<400> SEQUENCE: 45

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Gly
            20                  25                  30

Gly Ser Val Ala Trp Tyr Gln Gln Lys Pro Gly Lys Ala Pro Lys Leu
        35                  40                  45

Leu Ile Ser Phe Pro Gly Gly Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Phe Ser Trp
                85                  90                  95

Pro Ile Thr Phe Gly Gln Gly Thr Lys Val Glu Ile Lys Arg
            100                 105                 110

<210> SEQ ID NO 46
<211> LENGTH: 122
<212> TYPE: PRT
<213> ORGANISM: Artificial Sequence
<220> FEATURE:
<223> OTHER INFORMATION: synthesized_#11_VH

<400> SEQUENCE: 46

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Gln Asp Arg
            20                  25                  30

Met Ile His Trp Val Arg Gln Ala Pro Gly Lys Gly Leu Glu Trp Val
            35                  40                  45

Ala Ser Ile Leu Pro Phe Leu Gly Ala Thr Trp Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Trp Phe Ser Pro Phe Asp Tyr Trp Gly Gln Gly Thr Leu
            100                 105                 110

Val Thr Val Ser Ser Ala Ser Ala Ala Ala
            115                 120
```

```
<210> SEQ ID NO 47
<211> LENGTH: 110
<212> TYPE: PRT
<213> ORGANISM: Artificial Sequence
<220> FEATURE:
<223> OTHER INFORMATION: synthesized_#21_VL

<400> SEQUENCE: 47
```

```
Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Gly
            20                  25                  30

Ser Asn Val Ala Trp Tyr Gln Gln Lys Pro Gly Lys Ala Pro Lys Leu
        35                  40                  45

Leu Ile Phe Ser Ala Pro Phe Leu Tyr Ser Gly Val Pro Ser Arg Phe
        50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Phe Tyr Asp Trp
                85                  90                  95

Pro Leu Thr Phe Gly Gln Gly Thr Lys Val Glu Ile Lys Arg
            100                 105                 110
```

```
<210> SEQ ID NO 48
<211> LENGTH: 121
<212> TYPE: PRT
<213> ORGANISM: Artificial Sequence
<220> FEATURE:
<223> OTHER INFORMATION: synthesized_#21_VH

<400> SEQUENCE: 48
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asn Asn Gly
            20                  25                  30

Ser Ile His Trp Val Arg Gln Ala Pro Gly Lys Gly Leu Glu Trp Val
            35                  40                  45

Ala Trp Ile Trp Pro Phe Gly Gly Tyr Thr Tyr Tyr Ala Asp Ser Val
        50                  55                  60

Lys Gly Arg Phe Thr Ile Ser Ala Asp Thr Ser Lys Asn Thr Ala Tyr
65                  70                  75                  80
```

-continued

Leu Gln Met Asn Ser Leu Arg Ala Glu Asp Thr Ala Val Tyr Tyr Cys
                85                  90                  95

Ala Arg Gly Ser Tyr Gly Tyr Asp Tyr Trp Gly Gln Gly Thr Leu Val
            100                 105                 110

Thr Val Ser Ser Ala Ser Ala Ala Ala
        115                 120

<210> SEQ ID NO 49
<211> LENGTH: 110
<212> TYPE: PRT
<213> ORGANISM: Artificial Sequence
<220> FEATURE:
<223> OTHER INFORMATION: synthesized_#22_VL

<400> SEQUENCE: 49

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Asp
            20                  25                  30

Asp Asn Val Ala Trp Tyr Gln Gln Lys Pro Gly Lys Ala Pro Lys Leu
        35                  40                  45

Leu Ile Ser Ser Ser Ser Gly Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Asn Gly
                85                  90                  95

Pro Ile Thr Phe Gly Gln Gly Thr Lys Val Glu Ile Lys Arg
            100                 105                 110

<210> SEQ ID NO 50
<211> LENGTH: 121
<212> TYPE: PRT
<213> ORGANISM: Artificial Sequence
<220> FEATURE:
<223> OTHER INFORMATION: synthesized_#22_VH

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Gly
            20                  25                  30

Ser Ile His Trp Val Arg Gln Ala Pro Gly Lys Gly Leu Glu Trp Val
        35                  40                  45

Ala Ser Ile Trp Pro Phe Gly Gly Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Phe Gly Ser Asp Tyr Trp Gly Gln Gly Thr Leu Val
            100                 105                 110

Thr Val Ser Ser Ala Ser Ala Ala Ala
        115                 120

<210> SEQ ID NO 51
<211> LENGTH: 110
<212> TYPE: PRT

```
<213> ORGANISM: Artificial Sequence
<220> FEATURE:
<223> OTHER INFORMATION: synthesized_#33_VL

<400> SEQUENCE: 51

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Tyr
            20                  25                  30

Ser Ser Val Ala Trp Tyr Gln Gln Lys Pro Gly Lys Ala Pro Lys Leu
        35                  40                  45

Leu Ile Phe Gly Ser Ser Phe Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Tyr Asp Trp
                85                  90                  95

Pro Ile Thr Phe Gly Gln Gly Thr Lys Val Glu Ile Lys Arg
            100                 105                 110

<210> SEQ ID NO 52
<211> LENGTH: 121
<212> TYPE: PRT
<213> ORGANISM: Artificial Sequence
<220> FEATURE:
<223> OTHER INFORMATION: synthesized_#33_VH

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asn Asn Gly
            20                  25                  30

Gly Ile His Trp Val Arg Gln Ala Pro Gly Lys Gly Leu Glu Trp Val
        35                  40                  45

Ala Gly Ile Trp Pro Phe Trp Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Tyr Gly Phe Asp Tyr Trp Gly Gln Gly Thr Leu Val
            100                 105                 110

Thr Val Ser Ser Ala Ser Ala Ala Ala
        115                 120

<210> SEQ ID NO 53
<211> LENGTH: 110
<212> TYPE: PRT
<213> ORGANISM: Artificial Sequence
<220> FEATURE:
<223> OTHER INFORMATION: synthesized_#36_VL

<400> SEQUENCE: 53

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Thr
            20                  25                  30

Thr Thr Val Ala Trp Tyr Gln Gln Lys Pro Gly Lys Ala Pro Lys Leu
        35                  40                  45
```

-continued

```
Leu Ile Asn Lys Gly Ser Trp Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Asn Lys Trp
                85                  90                  95

Pro Leu Thr Phe Gly Gln Gly Thr Lys Val Glu Ile Lys Arg
            100                 105                 110

<210> SEQ ID NO 54
<211> LENGTH: 121
<212> TYPE: PRT
<213> ORGANISM: Artificial Sequence
<220> FEATURE:
<223> OTHER INFORMATION: synthesized_#36_VH

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asn Arg Tyr
            20                  25                  30

Ser Ile His Trp Val Arg Gln Ala Pro Gly Lys Gly Leu Glu Trp Val
        35                  40                  45

Ala Gly Ile Trp Pro Phe Gly Gly Asp Thr Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ala Thr Ser His Asp Tyr Trp Gly Gln Gly Thr Leu Val
            100                 105                 110

Thr Val Ser Ser Ala Ser Ala Ala Ala
        115                 120

<210> SEQ ID NO 55
<211> LENGTH: 114
<212> TYPE: PRT
<213> ORGANISM: Artificial Sequence
<220> FEATURE:
<223> OTHER INFORMATION: synthesized_#48_VL

<400> SEQUENCE: 55

Met Ala Asp Ile Gln Met Thr Gln Ser Pro Ser Ser Leu Ser Ala Ser
1               5                   10                  15

Val Gly Asp Arg Val Thr Ile Thr Cys Ser Gly Ser Ser Ser Asn Ile
            20                  25                  30

Gly Asp Asn Asn Val Tyr Trp Tyr Gln Gln Lys Pro Gly Lys Ala Pro
        35                  40                  45

Lys Leu Leu Ile Phe Gly Pro Ala Tyr Leu Tyr Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Ala Ala Gly Tyr
                85                  90                  95

Ser Asp Asn Asn Gly Ile Thr Phe Gly Gln Gly Thr Lys Val Glu Ile
            100                 105                 110

Lys Arg
```

-continued

<210> SEQ ID NO 56
<211> LENGTH: 126
<212> TYPE: PRT
<213> ORGANISM: Artificial Sequence
<220> FEATURE:
<223> OTHER INFORMATION: synthesized_#48_VH

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asn Phe
            20                  25                  30

Gly Ile His Trp Val Arg Gln Ala Pro Gly Lys Gly Leu Glu Trp Val
        35                  40                  45

Ala Gly Ile Trp Pro Tyr Gly Gly Tyr Thr Phe Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Asp Ser Tyr Ser Tyr Ser Gly Tyr Met Asp Tyr Trp Gly
            100                 105                 110

Gln Gly Thr Leu Val Thr Val Ser Ser Ala Ser Ala Ala Ala
        115                 120                 125

<210> SEQ ID NO 57
<211> LENGTH: 422
<212> TYPE: PRT
<213> ORGANISM: Artificial Sequence
<220> FEATURE:
<223> OTHER INFORMATION: synthesized_SARS-CoV-1-N protein

<400> SEQUENCE: 57

Met Ser Asp Asn Gly Pro Gln Ser Asn Gln Arg Ser Ala Pro Arg Ile
1               5                   10                  15

Thr Phe Gly Gly Pro Thr Asp Ser Thr Asp Asn Asn Gln Asn Gly Gly
            20                  25                  30

Arg Asn Gly Ala Arg Pro Lys Gln Arg Arg Pro Gln Gly Leu Pro Asn
        35                  40                  45

Asn Thr Ala Ser Trp Phe Thr Ala Leu Thr Gln His Gly Lys Glu Glu
    50                  55                  60

Leu Arg Phe Pro Arg Gly Gln Gly Val Pro Ile Asn Thr Asn Ser Gly
65                  70                  75                  80

Pro Asp Asp Gln Ile Gly Tyr Tyr Arg Arg Ala Thr Arg Arg Val Arg
                85                  90                  95

Gly Gly Asp Gly Lys Met Lys Glu Leu Ser Pro Arg Trp Tyr Phe Tyr
            100                 105                 110

Tyr Leu Gly Thr Gly Pro Glu Ala Ser Leu Pro Tyr Gly Ala Asn Lys
        115                 120                 125

Glu Gly Ile Val Trp Val Ala Thr Glu Gly Ala Leu Asn Thr Pro Lys
    130                 135                 140

Asp His Ile Gly Thr Arg Asn Pro Asn Asn Asn Ala Ala Thr Val Leu
145                 150                 155                 160

Gln Leu Pro Gln Gly Thr Thr Leu Pro Lys Gly Phe Tyr Ala Glu Gly
                165                 170                 175

Ser Arg Gly Gly Ser Gln Ala Ser Ser Arg Ser Ser Ser Arg Ser Arg

-continued

```
            180              185              190
Gly Asn Ser Arg Asn Ser Thr Pro Gly Ser Ser Arg Gly Asn Ser Pro
                195              200              205

Ala Arg Met Ala Ser Gly Gly Gly Glu Thr Ala Leu Ala Leu Leu Leu
    210              215              220

Leu Asp Arg Leu Asn Gln Leu Glu Ser Lys Val Ser Gly Lys Gly Gln
225              230              235              240

Gln Gln Gln Gly Gln Thr Val Thr Lys Lys Ser Ala Ala Glu Ala Ser
                245              250              255

Lys Lys Pro Arg Gln Lys Arg Thr Ala Thr Lys Gln Tyr Asn Val Thr
                260              265              270

Gln Ala Phe Gly Arg Arg Gly Pro Glu Gln Thr Gln Gly Asn Phe Gly
                275              280              285

Asp Gln Asp Leu Ile Arg Gln Gly Thr Asp Tyr Lys His Trp Pro Gln
                290              295              300

Ile Ala Gln Phe Ala Pro Ser Ala Ser Ala Phe Phe Gly Met Ser Arg
305              310              315              320

Ile Gly Met Glu Val Thr Pro Ser Gly Thr Trp Leu Thr Tyr His Gly
                325              330              335

Ala Ile Lys Leu Asp Asp Lys Asp Pro Gln Phe Lys Asp Asn Val Ile
                340              345              350

Leu Leu Asn Lys His Ile Asp Ala Tyr Lys Thr Phe Pro Pro Thr Glu
                355              360              365

Pro Lys Lys Asp Lys Lys Lys Lys Thr Asp Glu Ala Gln Pro Leu Pro
    370              375              380

Gln Arg Gln Lys Lys Gln Pro Thr Val Thr Leu Leu Pro Ala Ala Asp
385              390              395              400

Met Asp Asp Phe Ser Arg Gln Leu Gln Asn Ser Met Ser Gly Ala Ser
                405              410              415

Ala Asp Ser Thr Gln Ala
                420
```

```
<210> SEQ ID NO 58
<211> LENGTH: 419
<212> TYPE: PRT
<213> ORGANISM: Artificial Sequence
<220> FEATURE:
<223> OTHER INFORMATION: synthesized_SARS-CoV-2-N protein

<400> SEQUENCE: 58

Met Ser Asp Asn Gly Pro Gln Asn Gln Arg Asn Ala Pro Arg Ile Thr
1               5                10               15

Phe Gly Gly Pro Ser Asp Ser Thr Gly Ser Asn Gln Asn Gly Glu Arg
                20               25               30

Ser Gly Ala Arg Ser Lys Gln Arg Arg Pro Gln Gly Leu Pro Asn Asn
                35               40               45

Thr Ala Ser Trp Phe Thr Ala Leu Thr Gln His Gly Lys Glu Asp Leu
    50               55               60

Lys Phe Pro Arg Gly Gln Gly Val Pro Ile Asn Thr Asn Ser Ser Pro
65               70               75               80

Asp Asp Gln Ile Gly Tyr Tyr Arg Arg Ala Thr Arg Arg Ile Arg Gly
                85               90               95

Gly Asp Gly Lys Met Lys Asp Leu Ser Pro Arg Trp Tyr Phe Tyr Tyr
                100              105              110

Leu Gly Thr Gly Pro Glu Ala Gly Leu Pro Tyr Gly Ala Asn Lys Asp
```

-continued

```
            115                 120                 125

Gly Ile Ile Trp Val Ala Thr Glu Gly Ala Leu Asn Thr Pro Lys Asp
    130                 135                 140

His Ile Gly Thr Arg Asn Pro Ala Asn Asn Ala Ala Ile Val Leu Gln
145                 150                 155                 160

Leu Pro Gln Gly Thr Thr Leu Pro Lys Gly Phe Tyr Ala Glu Gly Ser
                165                 170                 175

Arg Gly Gly Ser Gln Ala Ser Ser Arg Ser Ser Ser Arg Ser Arg Asn
                180                 185                 190

Ser Ser Arg Asn Ser Thr Pro Gly Ser Ser Arg Gly Thr Ser Pro Ala
                195                 200                 205

Arg Met Ala Gly Asn Gly Gly Asp Ala Ala Leu Ala Leu Leu Leu Leu
    210                 215                 220

Asp Arg Leu Asn Gln Leu Glu Ser Lys Met Ser Gly Lys Gly Gln Gln
225                 230                 235                 240

Gln Gln Gly Gln Thr Val Thr Lys Lys Ser Ala Ala Glu Ala Ser Lys
                245                 250                 255

Lys Pro Arg Gln Lys Arg Thr Ala Thr Lys Ala Tyr Asn Val Thr Gln
                260                 265                 270

Ala Phe Gly Arg Arg Gly Pro Glu Gln Thr Gln Gly Asn Phe Gly Asp
                275                 280                 285

Gln Glu Leu Ile Arg Gln Gly Thr Asp Tyr Lys His Trp Pro Gln Ile
    290                 295                 300

Ala Gln Phe Ala Pro Ser Ala Ser Ala Phe Phe Gly Met Ser Arg Ile
305                 310                 315                 320

Gly Met Glu Val Thr Pro Ser Gly Thr Trp Leu Thr Tyr Thr Gly Ala
                325                 330                 335

Ile Lys Leu Asp Asp Lys Asp Pro Asn Phe Lys Asp Gln Val Ile Leu
                340                 345                 350

Leu Asn Lys His Ile Asp Ala Tyr Lys Thr Phe Pro Pro Thr Glu Pro
                355                 360                 365

Lys Lys Asp Lys Lys Lys Lys Ala Asp Glu Thr Gln Ala Leu Pro Gln
    370                 375                 380

Arg Gln Lys Lys Gln Gln Thr Val Thr Leu Leu Pro Ala Ala Asp Leu
385                 390                 395                 400

Asp Asp Phe Ser Lys Gln Leu Gln Gln Ser Met Ser Ser Ala Asp Ser
                405                 410                 415

Thr Gln Ala
```

```
<210> SEQ ID NO 59
<211> LENGTH: 413
<212> TYPE: PRT
<213> ORGANISM: Artificial Sequence
<220> FEATURE:
<223> OTHER INFORMATION: synthesized_MERS-CoV_N protein

<400> SEQUENCE: 59

Met Ala Ser Pro Ala Ala Pro Arg Ala Val Ser Phe Ala Asp Asn Asn
1               5                   10                  15

Asp Ile Thr Asn Thr Asn Leu Ser Arg Gly Arg Gly Arg Asn Pro Lys
                20                  25                  30

Pro Arg Ala Ala Pro Asn Asn Thr Val Ser Trp Tyr Thr Gly Leu Thr
        35                  40                  45

Gln His Gly Lys Val Pro Leu Thr Phe Pro Pro Gly Gln Gly Val Pro
    50                  55                  60
```

-continued

```
Leu Asn Ala Asn Ser Thr Pro Ala Gln Asn Ala Gly Tyr Trp Arg Arg
65                  70                  75                  80

Gln Asp Arg Lys Ile Asn Thr Gly Asn Gly Ile Lys Gln Leu Ala Pro
                85                  90                  95

Arg Trp Tyr Phe Tyr Tyr Thr Gly Thr Gly Pro Glu Ala Ala Leu Pro
                100                 105                 110

Phe Arg Ala Val Lys Asp Gly Ile Val Trp Val His Glu Asp Gly Ala
            115                 120                 125

Thr Asp Ala Pro Ser Thr Phe Gly Thr Arg Asn Pro Asn Asn Asp Ser
    130                 135                 140

Ala Ile Val Thr Gln Phe Ala Pro Gly Thr Lys Leu Pro Lys Asn Phe
145                 150                 155                 160

His Ile Glu Gly Thr Gly Gly Asn Ser Gln Ser Ser Ser Arg Ala Ser
                165                 170                 175

Ser Val Ser Arg Asn Ser Ser Arg Ser Ser Ser Gln Gly Ser Arg Ser
                180                 185                 190

Gly Asn Ser Thr Arg Gly Thr Ser Pro Gly Pro Ser Gly Ile Gly Ala
            195                 200                 205

Val Gly Gly Asp Leu Leu Tyr Leu Asp Leu Leu Asn Arg Leu Gln Ala
    210                 215                 220

Leu Glu Ser Gly Lys Val Lys Gln Ser Gln Pro Lys Val Ile Thr Lys
225                 230                 235                 240

Lys Asp Ala Ala Ala Ala Lys Asn Lys Met Arg His Lys Arg Thr Ser
                245                 250                 255

Thr Lys Ser Phe Asn Met Val Gln Ala Phe Gly Leu Arg Gly Pro Gly
                260                 265                 270

Asp Leu Gln Gly Asn Phe Gly Asp Leu Gln Leu Asn Lys Leu Gly Thr
            275                 280                 285

Glu Asp Pro Arg Trp Pro Gln Ile Ala Glu Leu Ala Pro Thr Ala Ser
    290                 295                 300

Ala Phe Met Gly Met Ser Gln Phe Lys Leu Thr His Gln Asn Asn Asp
305                 310                 315                 320

Asp His Gly Asn Pro Val Tyr Phe Leu Arg Tyr Ser Gly Ala Ile Lys
                325                 330                 335

Leu Asp Pro Lys Asn Pro Asn Tyr Asn Lys Trp Leu Glu Leu Leu Glu
                340                 345                 350

Gln Asn Ile Asp Ala Tyr Lys Thr Phe Pro Lys Lys Glu Lys Lys Gln
            355                 360                 365

Lys Ala Pro Lys Glu Glu Ser Thr Asp Gln Met Ser Glu Pro Pro Lys
    370                 375                 380

Glu Gln Arg Val Gln Gly Ser Ile Thr Gln Arg Thr Arg Thr Arg Pro
385                 390                 395                 400

Ser Val Gln Pro Gly Pro Met Ile Asp Val Asn Thr Asp
                405                 410
```

<210> SEQ ID NO 60
<211> LENGTH: 448
<212> TYPE: PRT
<213> ORGANISM: Artificial Sequence
<220> FEATURE:
<223> OTHER INFORMATION: synthesized_HCoV-OC43_N protein

<400> SEQUENCE: 60

```
Met Ser Phe Thr Pro Gly Lys Gln Ser Ser Ser Arg Ala Ser Ser Gly
1               5                   10                  15
```

-continued

```
Asn Arg Ser Gly Asn Gly Ile Leu Lys Trp Ala Asp Gln Ser Asp Gln
        20                  25                  30

Phe Arg Asn Val Gln Thr Arg Gly Arg Arg Ala Gln Pro Lys Gln Thr
        35                  40                  45

Ala Thr Ser Gln Gln Pro Ser Gly Gly Asn Val Val Pro Tyr Tyr Ser
    50                  55                  60

Trp Phe Ser Gly Ile Thr Gln Phe Gln Lys Gly Lys Glu Phe Glu Phe
65                  70                  75                  80

Val Glu Gly Gln Gly Val Pro Ile Ala Pro Gly Val Pro Ala Thr Glu
                85                  90                  95

Ala Lys Gly Tyr Trp Tyr Arg His Asn Arg Arg Ser Phe Lys Thr Ala
            100                 105                 110

Asp Gly Asn Gln Arg Gln Leu Leu Pro Arg Trp Tyr Phe Tyr Tyr Leu
        115                 120                 125

Gly Thr Gly Pro His Ala Lys Asp Gln Tyr Gly Thr Asp Ile Asp Gly
    130                 135                 140

Val Tyr Trp Val Ala Ser Asn Gln Ala Asp Val Asn Thr Pro Ala Asp
145                 150                 155                 160

Ile Val Asp Arg Asp Pro Ser Ser Asp Glu Ala Ile Pro Thr Arg Phe
                165                 170                 175

Pro Pro Gly Thr Val Leu Pro Gln Gly Tyr Tyr Ile Glu Gly Ser Gly
            180                 185                 190

Arg Ser Ala Pro Asn Ser Arg Ser Thr Ser Arg Thr Ser Ser Arg Ala
        195                 200                 205

Ser Ser Ala Gly Ser Arg Ser Arg Ala Asn Ser Gly Asn Arg Thr Pro
    210                 215                 220

Thr Ser Gly Val Thr Pro Asp Met Ala Asp Gln Ile Ala Ser Leu Val
225                 230                 235                 240

Leu Ala Lys Leu Gly Lys Asp Ala Thr Lys Pro Gln Gln Val Thr Lys
                245                 250                 255

His Thr Ala Lys Glu Val Arg Gln Lys Ile Leu Asn Lys Pro Arg Gln
            260                 265                 270

Lys Arg Ser Pro Asn Lys Gln Cys Thr Val Gln Gln Cys Phe Gly Lys
        275                 280                 285

Arg Gly Pro Asn Gln Asn Phe Gly Gly Gly Glu Met Leu Lys Leu Gly
    290                 295                 300

Thr Ser Asp Pro Gln Phe Pro Ile Leu Ala Glu Leu Ala Pro Thr Ala
305                 310                 315                 320

Gly Ala Phe Phe Phe Gly Ser Arg Leu Glu Leu Ala Lys Val Gln Asn
                325                 330                 335

Leu Ser Gly Asn Pro Asp Glu Pro Gln Lys Asp Val Tyr Glu Leu Arg
            340                 345                 350

Tyr Asn Gly Ala Ile Arg Phe Asp Ser Thr Leu Ser Gly Phe Glu Thr
        355                 360                 365

Ile Met Lys Val Leu Asn Glu Asn Leu Asn Ala Tyr Gln Gln Gln Asp
    370                 375                 380

Gly Met Met Asn Met Ser Pro Lys Pro Gln Arg Gln Arg Gly His Lys
385                 390                 395                 400

Asn Gly Gln Gly Glu Asn Asp Asn Ile Ser Val Ala Val Pro Lys Ser
                405                 410                 415

Arg Val Gln Gln Asn Lys Ser Arg Glu Leu Thr Ala Glu Asp Ile Ser
            420                 425                 430
```

```
Leu Leu Lys Lys Met Asp Glu Pro Tyr Thr Glu Asp Thr Ser Glu Ile
    435                 440                 445

<210> SEQ ID NO 61
<211> LENGTH: 389
<212> TYPE: PRT
<213> ORGANISM: Artificial Sequence
<220> FEATURE:
<223> OTHER INFORMATION: synthesized_HCoV-229E_N protein

<400> SEQUENCE: 61

Met Ala Thr Val Lys Trp Ala Asp Ala Ser Glu Pro Gln Arg Gly Arg
1               5                   10                  15

Gln Gly Arg Ile Pro Tyr Ser Leu Tyr Ser Pro Leu Leu Val Asp Ser
            20                  25                  30

Glu Gln Pro Trp Lys Val Ile Pro Arg Asn Leu Val Pro Ile Asn Lys
        35                  40                  45

Lys Asp Lys Asn Lys Leu Ile Gly Tyr Trp Asn Val Gln Lys Arg Phe
    50                  55                  60

Arg Thr Arg Lys Gly Lys Arg Val Asp Leu Ser Pro Lys Leu His Phe
65                  70                  75                  80

Tyr Tyr Leu Gly Thr Gly Pro His Lys Asp Ala Lys Phe Arg Glu Arg
                85                  90                  95

Val Glu Gly Val Val Trp Val Ala Val Asp Gly Ala Lys Thr Glu Pro
            100                 105                 110

Thr Gly Tyr Gly Val Arg Arg Lys Asn Ser Glu Pro Glu Ile Pro His
        115                 120                 125

Phe Asn Gln Lys Leu Pro Asn Gly Val Thr Val Val Glu Glu Pro Asp
    130                 135                 140

Ser Arg Ala Pro Ser Arg Ser Gln Ser Arg Ser Gln Ser Arg Gly Arg
145                 150                 155                 160

Gly Glu Ser Lys Pro Gln Ser Arg Asn Pro Ser Ser Asp Arg Asn His
            165                 170                 175

Asn Ser Gln Asp Asp Ile Met Lys Ala Val Ala Ala Ala Leu Lys Ser
            180                 185                 190

Leu Gly Phe Asp Lys Pro Gln Glu Lys Asp Lys Lys Ser Ala Lys Thr
        195                 200                 205

Gly Thr Pro Lys Pro Ser Arg Asn Gln Ser Pro Ala Ser Ser Gln Thr
    210                 215                 220

Ser Ala Lys Ser Leu Ala Arg Ser Gln Ser Ser Glu Thr Lys Glu Gln
225                 230                 235                 240

Lys His Glu Met Gln Lys Pro Arg Trp Lys Arg Gln Pro Asn Asp Asp
            245                 250                 255

Val Thr Ser Asn Val Thr Gln Cys Phe Gly Pro Arg Asp Leu Asp His
            260                 265                 270

Asn Phe Gly Ser Ala Gly Val Val Ala Asn Gly Val Lys Ala Lys Gly
        275                 280                 285

Tyr Pro Gln Phe Ala Glu Leu Val Pro Ser Thr Ala Ala Met Leu Phe
    290                 295                 300

Asp Ser His Ile Val Ser Lys Glu Ser Gly Asn Thr Val Val Leu Thr
305                 310                 315                 320

Phe Thr Thr Arg Val Thr Val Ser Lys Asp His Pro His Leu Gly Lys
                325                 330                 335

Phe Leu Glu Glu Leu Asn Ala Phe Thr Arg Glu Met Gln Gln His Pro
            340                 345                 350
```

-continued

```
Leu Leu Asn Pro Ser Ala Leu Glu Phe Asn Pro Ser Gln Thr Ser Pro
        355             360             365

Ala Thr Ala Glu Pro Val Arg Asp Glu Val Ser Ile Glu Thr Asp Ile
        370             375             380

Ile Asp Glu Val Asn
385

<210> SEQ ID NO 62
<211> LENGTH: 377
<212> TYPE: PRT
<213> ORGANISM: Artificial Sequence
<220> FEATURE:
<223> OTHER INFORMATION: synthesized_HCoV-NL63

<400> SEQUENCE: 62

Met Ala Ser Val Asn Trp Ala Asp Asp Arg Ala Ala Arg Lys Lys Phe
1               5               10              15

Pro Pro Pro Ser Phe Tyr Met Pro Leu Leu Val Ser Ser Asp Lys Ala
                20              25              30

Pro Tyr Arg Val Ile Pro Arg Asn Leu Val Pro Ile Gly Lys Gly Asn
        35              40              45

Lys Asp Glu Gln Ile Gly Tyr Trp Asn Val Gln Glu Arg Trp Arg Met
    50              55              60

Arg Arg Gly Gln Arg Val Asp Leu Pro Pro Lys Val His Phe Tyr Tyr
65              70              75              80

Leu Gly Thr Gly Pro His Lys Asp Leu Lys Phe Arg Gln Arg Ser Asp
                85              90              95

Gly Val Val Trp Val Ala Lys Glu Gly Ala Lys Thr Val Asn Thr Ser
                100             105             110

Leu Gly Asn Arg Lys Arg Asn Gln Lys Pro Leu Glu Pro Lys Phe Ser
        115             120             125

Ile Ala Leu Pro Pro Glu Leu Ser Val Val Glu Phe Glu Asp Arg Ser
        130             135             140

Asn Asn Ser Ser Arg Ala Ser Ser Arg Ser Ser Thr Arg Asn Asn Ser
145             150             155             160

Arg Asp Ser Ser Arg Ser Thr Ser Arg Gln Gln Ser Arg Thr Arg Ser
                165             170             175

Asp Ser Asn Gln Ser Ser Ser Asp Leu Val Ala Ala Val Thr Leu Ala
                180             185             190

Leu Lys Asn Leu Gly Phe Asp Asn Gln Ser Lys Ser Pro Ser Ser Ser
        195             200             205

Gly Thr Ser Thr Pro Lys Lys Pro Asn Lys Pro Leu Ser Gln Pro Arg
        210             215             220

Ala Asp Lys Pro Ser Gln Leu Lys Lys Pro Arg Trp Lys Arg Val Pro
225             230             235             240

Thr Arg Glu Glu Asn Val Ile Gln Cys Phe Gly Pro Arg Asp Phe Asn
                245             250             255

His Asn Met Gly Asp Ser Asp Leu Val Gln Asn Gly Val Asp Ala Lys
                260             265             270

Gly Phe Pro Gln Leu Ala Glu Leu Ile Pro Asn Gln Ala Ala Leu Phe
        275             280             285

Phe Asp Ser Glu Val Ser Thr Asp Glu Val Gly Asp Asn Val Gln Ile
        290             295             300

Thr Tyr Thr Tyr Lys Met Leu Val Ala Lys Asp Asn Lys Asn Leu Pro
305             310             315             320
```

-continued

```
Lys Phe Ile Glu Gln Ile Ser Ala Phe Thr Lys Pro Ser Ser Ile Lys
                325                 330                 335

Glu Met Gln Ser Gln Ser Ser His Val Ala Gln Asn Thr Val Leu Asn
                340                 345                 350

Ala Ser Ile Pro Glu Ser Lys Pro Leu Ala Asp Asp Asp Ser Ala Ile
                355                 360                 365

Ile Glu Ile Val Asn Glu Val Leu His
                370                 375

<210> SEQ ID NO 63
<211> LENGTH: 441
<212> TYPE: PRT
<213> ORGANISM: Artificial Sequence
<220> FEATURE:
<223> OTHER INFORMATION: synthesized_HCoV-HKU1

<400> SEQUENCE: 63

Met Ser Tyr Thr Pro Gly His Tyr Ala Gly Ser Arg Ser Ser Gly
1               5                   10                  15

Asn Arg Ser Gly Ile Leu Lys Lys Thr Ser Trp Ala Asp Gln Ser Glu
                20                  25                  30

Arg Asn Tyr Gln Thr Phe Asn Arg Gly Arg Lys Thr Gln Pro Lys Phe
                35                  40                  45

Thr Val Ser Thr Gln Pro Gln Gly Asn Thr Ile Pro His Tyr Ser Trp
                50                  55                  60

Phe Ser Gly Ile Thr Gln Phe Gln Lys Gly Arg Asp Phe Lys Phe Ser
65                  70                  75                  80

Asp Gly Gln Gly Val Pro Ile Ala Phe Gly Val Pro Pro Ser Glu Ala
                85                  90                  95

Lys Gly Tyr Trp Tyr Arg His Ser Arg Arg Ser Phe Lys Thr Ala Asp
                100                 105                 110

Gly Gln Gln Lys Gln Leu Leu Pro Arg Trp Tyr Phe Tyr Tyr Leu Gly
                115                 120                 125

Thr Gly Pro Tyr Ala Asn Ala Ser Tyr Gly Glu Ser Leu Glu Gly Val
                130                 135                 140

Phe Trp Val Ala Asn His Gln Ala Asp Thr Ser Thr Pro Ser Asp Val
145                 150                 155                 160

Ser Ser Arg Asp Pro Thr Thr Gln Glu Ala Ile Pro Thr Arg Phe Pro
                165                 170                 175

Pro Gly Thr Ile Leu Pro Gln Gly Tyr Tyr Val Glu Gly Ser Gly Arg
                180                 185                 190

Ser Ala Ser Asn Ser Arg Pro Gly Ser Arg Ser Gln Ser Arg Gly Pro
                195                 200                 205

Asn Asn Arg Ser Leu Ser Arg Ser Asn Ser Asn Phe Arg His Ser Asp
                210                 215                 220

Ser Ile Val Lys Pro Asp Met Ala Asp Glu Ile Ala Asn Leu Val Leu
225                 230                 235                 240

Ala Lys Leu Gly Lys Glu Ser Lys Pro Gln Gln Val Thr Lys Gln Asn
                245                 250                 255

Ala Lys Glu Ile Arg His Lys Ile Leu Thr Lys Pro Arg Gln Lys Arg
                260                 265                 270

Thr Pro Asn Lys His Cys Asn Val Gln Gln Cys Phe Gly Lys Arg Gly
                275                 280                 285

Pro Ser Gln Asn Phe Gly Asn Ala Glu Met Leu Lys Leu Gly Thr Asn
                290                 295                 300
```

-continued

```
Asp Pro Gln Phe Pro Ile Leu Ala Glu Leu Ala Pro Thr Pro Gly Ala
305             310             315             320

Phe Phe Phe Gly Ser Lys Leu Glu Leu Val Lys Arg Glu Ser Glu Ala
                325             330             335

Asp Ser Pro Val Lys Asp Val Phe Glu Leu Arg Tyr Ser Gly Ser Ile
            340             345             350

Arg Phe Asp Ser Thr Leu Pro Gly Phe Glu Thr Ile Met Lys Val Leu
        355             360             365

Lys Glu Asn Leu Asp Ala Tyr Val Asn Ser Asn Gln Asn Thr Val Ser
    370             375             380

Gly Ser Leu Ser Pro Lys Pro Gln Arg Lys Arg Gly Val Lys Gln Ser
385             390             395             400

Pro Glu Leu Phe Asp Ser Leu Asn Leu Ser Ala Asp Thr Gln His Ile
            405             410             415

Ser Asn Asp Phe Thr Pro Glu Asp His Ser Leu Leu Ala Thr Leu Asp
            420             425             430

Asp Pro Tyr Val Glu Asp Ser Val Ala
        435             440
```

```
<210> SEQ ID NO 64
<211> LENGTH: 36
<212> TYPE: PRT
<213> ORGANISM: Artificial Sequence
<220> FEATURE:
<223> OTHER INFORMATION: synthesized_F primer

<400> SEQUENCE: 64

Cys Gly Thr Gly Thr Cys Gly Cys Ala Thr Cys Thr Gly Ala Ala Gly
1               5               10              15

Thr Gly Cys Ala Gly Cys Thr Gly Gly Thr Gly Gly Ala Ala Thr Cys
                20              25              30

Gly Gly Gly Ala
        35
```

```
<210> SEQ ID NO 65
<211> LENGTH: 48
<212> TYPE: PRT
<213> ORGANISM: Artificial Sequence
<220> FEATURE:
<223> OTHER INFORMATION: synthesized_R primer

<400> SEQUENCE: 65

Gly Ala Cys Cys Gly Ala Thr Gly Gly Gly Cys Cys Cys Thr Thr Gly
1               5               10              15

Gly Thr Gly Cys Thr Ala Gly Cys Cys Gly Ala Gly Cys Thr Cys Ala
                20              25              30

Cys Gly Gly Thr Ala Ala Cys Ala Ala Gly Gly Gly Thr Gly Cys Cys
        35              40                      45
```

```
<210> SEQ ID NO 66
<211> LENGTH: 59
<212> TYPE: PRT
<213> ORGANISM: Artificial Sequence
<220> FEATURE:
<223> OTHER INFORMATION: synthesized_F primer

<400> SEQUENCE: 66

Cys Ala Gly Gly Thr Gly Cys Ala Cys Gly Ala Thr Gly Thr Gly Ala
1               5               10              15

Thr Gly Gly Thr Ala Cys Cys Gly Ala Thr Ala Thr Thr Cys Ala Ala
```

-continued

```
                20                  25                  30

Ala Thr Gly Ala Cys Cys Cys Ala Gly Ala Gly Cys Cys Cys Gly Ala
            35                  40                  45

Gly Cys Ala Gly Cys Cys Thr Gly Ala Gly Cys
        50                  55

<210> SEQ ID NO 67
<211> LENGTH: 36
<212> TYPE: PRT
<213> ORGANISM: Artificial Sequence
<220> FEATURE:
<223> OTHER INFORMATION: synthesized_R primer

<400> SEQUENCE: 67

Thr Gly Cys Ala Gly Cys Cys Ala Cys Cys Gly Thr Ala Cys Gly Thr
1               5                   10                  15

Thr Thr Gly Ala Thr Thr Thr Cys Cys Ala Cys Cys Thr Thr Gly Gly
            20                  25                  30

Thr Gly Cys Cys
        35
```